US007851668B2

(12) United States Patent
Elder et al.

(10) Patent No.: US 7,851,668 B2
(45) Date of Patent: Dec. 14, 2010

(54) ABSORBENT ARTICLE AND METHOD FOR MAINTAINING OR IMPROVING SKIN HEALTH

(75) Inventors: Gretchen Louise Elder, Blue Ash, OH (US); Donald Carroll Roe, West Chester, OH (US); Thomas James Klofta, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/472,019

(22) Filed: Jun. 21, 2006

(65) Prior Publication Data

US 2006/0241554 A1  Oct. 26, 2006

Related U.S. Application Data

(60) Continuation of application No. 10/027,295, filed on Dec. 20, 2001, now abandoned, which is a division of application No. 08/926,532, filed on Sep. 10, 1997, now Pat. No. 6,803,496, which is a continuation of application No. 08/884,069, filed on Jun. 27, 1997, now Pat. No. 6,118,041, which is a continuation of application No. 08/345,159, filed on Nov. 28, 1994, now Pat. No. 5,643,588.

(51) Int. Cl.
*A61F 13/15* (2006.01)
*A61L 9/00* (2006.01)
*A61L 9/04* (2006.01)

(52) U.S. Cl. .................. 604/367; 604/359; 604/360; 604/361; 604/364; 424/76.1; 424/76.4

(58) Field of Classification Search .................. 604/359, 604/360, 361, 367, 364; 424/76.1, 76.4, 424/76.21
See application file for complete search history.

(56) References Cited

U.S. PATENT DOCUMENTS

| 2,804,424 A | 8/1957 | Stirn et al. |
|---|---|---|
| 3,464,413 A | 9/1969 | Goldfarb et al. |
| 3,489,148 A | 1/1970 | Duncan et al. |
| 3,490,454 A | 1/1970 | Goldfarb et al. |
| 3,567,820 A | 3/1971 | Sperti |
| 3,585,998 A | 6/1971 | Hayford et al. |
| 3,848,594 A | 11/1974 | Buell |
| 3,860,003 A | 1/1975 | Buell |
| 3,875,942 A | 4/1975 | Roberts et al. |
| 3,896,807 A | 7/1975 | Buchalter |
| 3,902,493 A | 9/1975 | Baier et al. |
| 3,911,173 A | 10/1975 | Sprague et al. |

(Continued)

FOREIGN PATENT DOCUMENTS

CA        2019557        12/1990

(Continued)

*Primary Examiner*—Jacqueline F. Stephens
(74) *Attorney, Agent, or Firm*—Amy M. Foust; Charles R. Ware

(57) ABSTRACT

Disclosed is a method for maintaining and/or improving skin health in the area of a wearer covered by an absorbent article. The absorbent article includes a vapor permeable backsheet, a liquid pervious topsheet positioned in facing relation with the backsheet, an absorbent core located between the backsheet and the topsheet. The absorbent article also includes skin care compositions thereon for maintaining and/or improving skin health.

5 Claims, 7 Drawing Sheets

U.S. PATENT DOCUMENTS

| | | |
|---|---|---|
| 3,920,015 A | 11/1975 | Wortham |
| 3,929,135 A | 12/1975 | Thompson |
| 3,935,862 A | 2/1976 | Kraskin |
| 4,011,389 A | 3/1977 | Langdon et al. |
| 4,034,077 A | 7/1977 | Hill et al. |
| 4,112,167 A | 9/1978 | Dake et al. |
| 4,138,416 A | 2/1979 | Koresawa et al. |
| 4,253,461 A | 3/1981 | Strickland et al. |
| 4,263,363 A | 4/1981 | Buck et al. |
| 4,324,246 A | 4/1982 | Mullane et al. |
| 4,324,247 A | 4/1982 | Aziz |
| 4,342,314 A | 8/1982 | Radel et al. |
| 4,381,781 A | 5/1983 | Sciaraffa et al. |
| 4,463,045 A | 7/1984 | Ahr et al. |
| 4,513,051 A | 4/1985 | Lavash |
| 4,515,595 A | 5/1985 | Kievit et al. |
| 4,556,146 A | 12/1985 | Swanson et al. |
| 4,556,560 A | 12/1985 | Buckingham |
| 4,569,343 A | 2/1986 | Kimura et al. |
| 4,573,986 A | 3/1986 | Minetola et al. |
| 4,578,069 A | 3/1986 | Whitehead et al. |
| 4,589,876 A | 5/1986 | Van Tilburg |
| 4,597,760 A | 7/1986 | Buell |
| 4,597,761 A | 7/1986 | Buell |
| 4,609,518 A | 9/1986 | Curro et al. |
| 4,610,678 A | 9/1986 | Weisman et al. |
| 4,623,339 A | 11/1986 | Ciraldo et al. |
| 4,629,643 A | 12/1986 | Curro et al. |
| 4,648,876 A | 3/1987 | Becker et al. |
| 4,657,537 A | 4/1987 | Zimmerer |
| 4,662,875 A | 5/1987 | Hirotsu et al. |
| 4,666,765 A | 5/1987 | Caldwell et al. |
| 4,673,402 A | 6/1987 | Weisman et al. |
| 4,685,909 A | 8/1987 | Berg et al. |
| 4,687,478 A | 8/1987 | Van tilburg |
| 4,690,821 A | 9/1987 | Smith et al. |
| 4,692,161 A | 9/1987 | Puletti et al. |
| 4,695,278 A | 9/1987 | Lawson |
| 4,704,112 A | 11/1987 | Suzuki et al. |
| 4,704,115 A | 11/1987 | Buell |
| 4,713,068 A | 12/1987 | Wang |
| 4,718,898 A | 1/1988 | Puletti et al. |
| 4,753,643 A | 6/1988 | Kassai |
| 4,758,239 A | 7/1988 | Yeo et al. |
| 4,785,996 A | 11/1988 | Ziecker et al. |
| 4,790,836 A | 12/1988 | Brecher |
| 4,795,454 A | 1/1989 | Dragoo |
| 4,828,556 A | 5/1989 | Braun et al. |
| 4,833,172 A | 5/1989 | Schwarz et al. |
| 4,834,735 A | 5/1989 | Alemany et al. |
| 4,842,593 A | 6/1989 | Jordan et al. |
| 4,842,666 A | 6/1989 | Werenicz et al. |
| 4,846,815 A | 7/1989 | Scripps |
| 4,857,067 A | 8/1989 | Wood et al. |
| 4,882,204 A | 11/1989 | Tenenbaum |
| 4,888,231 A | 12/1989 | Angstadt |
| 4,894,060 A | 1/1990 | Nestegard |
| 4,900,317 A | 2/1990 | Buell |
| 4,902,553 A | 2/1990 | Hwang et al. |
| 4,904,524 A | 2/1990 | Yoh |
| 4,909,802 A | 3/1990 | Ahr et al. |
| 4,909,803 A | 3/1990 | Aziz et al. |
| 4,911,932 A | 3/1990 | Clum et al. |
| 4,923,650 A | 5/1990 | Antoon et al. |
| 4,929,498 A | 5/1990 | Suskind et al. |
| 4,934,535 A | 6/1990 | Muckenfuhs et al. |
| 4,938,753 A | 7/1990 | Van Gompel et al. |
| 4,940,464 A | 7/1990 | Van Gompel et al. |
| 4,946,527 A | 8/1990 | Battrell |
| 4,950,254 A | 8/1990 | Anderson et al. |
| 4,950,264 A | 8/1990 | Osborn, III |
| 4,959,059 A | 9/1990 | Eilender et al. |
| 4,963,591 A * | 10/1990 | Fourman et al. ............ 514/781 |
| 4,964,860 A | 10/1990 | Gipson et al. |
| 4,979,300 A | 12/1990 | Blank et al. |
| 4,988,344 A | 1/1991 | Reising et al. |
| 4,988,345 A | 1/1991 | Reising et al. |
| 4,990,144 A | 2/1991 | Blott |
| 4,996,238 A | 2/1991 | Matravers |
| 5,006,394 A | 4/1991 | Baird |
| 5,008,296 A | 4/1991 | Antoon et al. |
| 5,009,653 A | 4/1991 | Osborn, III |
| 5,011,698 A | 4/1991 | Antoon et al. |
| 5,026,364 A | 6/1991 | Robertson |
| 5,034,444 A | 7/1991 | Yun et al. |
| 5,043,155 A | 8/1991 | Puchalski et al. |
| 5,059,282 A | 10/1991 | Ampulski et al. |
| 5,091,193 A | 2/1992 | Enjolras et al. |
| 5,092,861 A | 3/1992 | Nomura et al. |
| 5,102,597 A | 4/1992 | Roe et al. |
| 5,147,345 A | 9/1992 | Young et al. |
| 5,151,092 A | 9/1992 | Buell et al. |
| 5,194,261 A | 3/1993 | Pichierri |
| 5,202,173 A | 4/1993 | Wu et al. |
| 5,221,274 A | 6/1993 | Buell et al. |
| 5,234,423 A | 8/1993 | Alemmany et al. |
| 5,246,433 A | 9/1993 | Hasse et al. |
| 5,254,111 A | 10/1993 | Wu et al. |
| 5,264,460 A | 11/1993 | Jakobson et al. |
| 5,267,992 A | 12/1993 | Van Tilberg |
| 5,296,184 A | 3/1994 | Wu et al. |
| 5,321,098 A | 6/1994 | Lal |
| 5,362,488 A | 11/1994 | Sibley et al. |
| 5,370,132 A | 12/1994 | Weber et al. |
| 5,376,655 A | 12/1994 | Imaki et al. |
| 5,389,094 A | 2/1995 | Lavash et al. |
| 5,399,174 A | 3/1995 | Yeo et al. |
| 5,409,903 A | 4/1995 | Polak et al. |
| 5,413,568 A | 5/1995 | Roach et al. |
| 5,415,649 A | 5/1995 | Watanabe et al. |
| 5,436,007 A | 7/1995 | Hartung et al. |
| 5,444,096 A | 8/1995 | McCrea et al. |
| 5,460,623 A | 10/1995 | Emenaker et al. |
| 5,489,283 A | 2/1996 | Van Tilberg |
| 5,492,751 A | 2/1996 | Butt et al. |
| 5,509,915 A | 4/1996 | Hanson et al. |
| 5,525,345 A | 6/1996 | Warner et al. |
| 5,525,346 A | 6/1996 | Hartung et al. |
| 5,554,145 A | 9/1996 | Roe et al. |
| 5,558,655 A | 9/1996 | Jezzi et al. |
| 5,569,231 A | 10/1996 | Emenaker et al. |
| 5,569,234 A | 10/1996 | Buell et al. |
| 5,595,723 A | 1/1997 | Quay |
| 5,599,420 A | 2/1997 | Yeo et al. |
| 5,607,760 A | 3/1997 | Roe et al. |
| 5,609,587 A | 3/1997 | Roe |
| 5,618,522 A | 4/1997 | Kaleta et al. |
| 5,618,529 A | 4/1997 | Pichierri |
| 5,620,430 A | 4/1997 | Bamber |
| 5,628,737 A | 5/1997 | Dobrin et al. |
| 5,635,191 A | 6/1997 | Roe et al. |
| 5,643,588 A | 7/1997 | Roe et al. |
| 5,695,868 A | 12/1997 | McCormick et al. |
| 5,762,641 A | 6/1998 | Plischke et al. |
| 5,833,967 A | 11/1998 | Ramin |
| 5,836,929 A | 11/1998 | Plischke et al. |
| 5,855,898 A | 1/1999 | Baines et al. |
| 5,855,999 A | 1/1999 | McCormack et al. |
| 5,871,763 A | 2/1999 | Luu et al. |
| 5,968,025 A | 10/1999 | Roe et al. |
| 5,998,695 A | 12/1999 | Roe et al. |
| 6,107,537 A | 8/2000 | Elder et al. |
| 6,108,093 A | 8/2000 | Berman |
| 6,118,041 A | 9/2000 | Roe et al. |

| | | |
|---|---|---|
| 6,120,488 A | 9/2000 | Vanrijswijck et al. |
| 6,120,783 A | 9/2000 | Roe et al. |
| 6,153,209 A | 11/2000 | Vega et al. |
| 6,156,024 A | 12/2000 | Schulte et al. |
| 6,166,285 A | 12/2000 | Schulte et al. |
| 6,204,208 B1 | 3/2001 | Krzysik et al. |
| 6,217,890 B1 | 4/2001 | Paul et al. |
| 6,270,487 B1 | 8/2001 | Sheehan et al. |
| 6,287,581 B1 | 9/2001 | Krzysik et al. |
| 6,290,979 B1 | 9/2001 | Roe et al. |
| 6,296,862 B1 | 10/2001 | Paul et al. |
| 6,316,013 B1 | 11/2001 | Paul et al. |
| 6,426,444 B2 | 7/2002 | Roe et al. |
| 6,476,288 B1 | 11/2002 | Vanrijswijck et al. |
| 6,498,284 B1 | 12/2002 | Roe |
| 6,504,028 B2 | 1/2003 | Fossum et al. |
| 6,541,629 B1 | 4/2003 | Osborne et al. |
| 6,570,054 B1 | 5/2003 | Gatto et al. |
| 6,586,652 B1 | 7/2003 | Roe et al. |
| 6,624,341 B1 | 9/2003 | Depner et al. |
| 6,627,787 B1 | 9/2003 | Roe et al. |
| 6,639,119 B2 | 10/2003 | Roe et al. |
| 6,703,536 B2 | 3/2004 | Roe et al. |
| 6,710,223 B1 | 3/2004 | Van Rijswijck et al. |
| 6,716,441 B1 | 4/2004 | Osborne et al. |
| 6,723,788 B1 | 4/2004 | Osborne et al. |
| 6,793,930 B2 | 9/2004 | Gatto et al. |
| 6,825,393 B2 | 11/2004 | Roe et al. |
| 6,861,571 B1 | 3/2005 | Roe et al. |
| 7,005,557 B2 | 2/2006 | Klofta et al. |
| 7,033,645 B2 | 4/2006 | Gatto et al. |
| 7,166,292 B2 | 1/2007 | Isele et al. |
| 2001/0053902 A1 | 12/2001 | Roe et al. |
| 2002/0143304 A1 | 10/2002 | Elder et al. |
| 2002/0147433 A1 | 10/2002 | Mcosker et al. |
| 2002/0165508 A1 | 11/2002 | Klofta et al. |
| 2003/0035824 A1 | 2/2003 | Isele |
| 2003/0077307 A1 | 4/2003 | Klofta et al. |
| 2003/0082219 A1 | 5/2003 | Warren et al. |
| 2003/0139711 A1 | 7/2003 | Roe et al. |
| 2003/0167043 A1 | 9/2003 | Roe et al. |
| 2003/0195486 A1 | 10/2003 | Gatto et al. |
| 2004/0039362 A1 | 2/2004 | Roe et al. |
| 2004/0175343 A1 | 9/2004 | Osborne et al. |
| 2004/0193126 A1 | 9/2004 | Roe et al. |
| 2004/0208984 A1 | 10/2004 | Gatto et al. |
| 2005/0208112 A1 | 9/2005 | Roe et al. |
| 2005/0208113 A1 | 9/2005 | Roe et al. |
| 2006/0135920 A1 | 6/2006 | Virgilio et al. |
| 2006/0206077 A1 | 9/2006 | Warren et al. |
| 2006/0241554 A1 | 10/2006 | Elder et al. |
| 2007/0219515 A1 | 9/2007 | Marsh et al. |

FOREIGN PATENT DOCUMENTS

| | | |
|---|---|---|
| DE | 4136540 | 5/1992 |
| EP | 0 238 200 | 9/1987 |
| EP | 0 315 013 | 10/1988 |
| EP | 0 297 828 A1 | 1/1989 |
| EP | 0 564 307 A1 | 10/1993 |
| EP | 0 692 263 B1 | 1/1996 |
| FR | 2714603 A1 | 7/1995 |
| GB | 2 033 751 A | 5/1980 |
| GB | 2 311 727 A | 8/1997 |
| JP | 61-028078 | 2/1986 |
| JP | 02-31756 | 2/1990 |
| JP | 04-182423 | 6/1992 |
| JP | 05-285170 | 11/1993 |
| JP | 08-52175 | 2/1996 |
| WO | WO 92/11830 | 7/1992 |
| WO | WO 95/16746 | 6/1995 |
| WO | WO 96/16682 | 6/1996 |
| WO | WO 98/24390 | 6/1998 |
| WO | WO 01/00156 A1 | 1/2001 |

* cited by examiner

ABSORBENT ARTICLE AND METHOD FOR MAINTAINING OR IMPROVING SKIN HEALTH

This application is a continuation of U.S. application Ser. No. 10/027,295 filed on Dec. 20, 2001; now abandoned which is a divisional of U.S. application Ser. No. 08/926,532, filed on Sep. 10, 1997 by Elder et al., now U.S. Pat. No. 6,803,496; which is a continuation of U.S. application Ser. No. 08/884,069, filed on Jun. 27, 1997, now U.S. Pat. No. 6,118,041; which is a continuation of U.S. application Ser. No. 08/345,159, filed on Nov. 28, 1994, now U.S. Pat. No. 5,643,588.

TECHNICAL FIELD

This application relates to a method for maintaining or improving skin health in wearers of absorbent articles such as diapers, training pants, adult incontinence devices, feminine hygiene products, and the like. More particularly, the application relates to a method comprising the repeated use of absorbent articles that deliver a composition to the wearer's skin, so as to provide a skin protective barrier and/or a therapeutic benefit.

BACKGROUND OF THE INVENTION

Many types of disposable absorbent products, such as diapers, are available that have a high capacity for absorbing urine and other body exudates. Disposable products of this type generally comprise some sort of liquid-pervious topsheet material, an absorbent core, and a liquid-impervious backsheet material. Although these types of absorbent structures may be highly efficient for the absorption of liquids, it is well recognized that long-term wear of such structures may lead to skin which is compromised in terms of being over hydrated or exposed to skin irritants commonly found in body exudates. It is generally known that skin under absorbent articles is more susceptible to skin disorders, including diaper rash, erythema (i.e., redness), heat rash, abrasion, pressure marks and skin barrier loss. For example, 21 C.F.R. 333.503 defines diaper rash as "[a]n inflammatory skin condition in the diaper area (perineum, buttocks, lower abdomen, and inner thighs) caused by one or more of the following factors: moisture, occlusion, chafing, continued contact with urine or feces or both, or mechanical or chemical irritation."

To address the concerns of skin disorders associated with wearing absorbent articles, the caregiver often applies skin protective products such as Vaseline®, medicated ointments, powders, etc. to the buttocks, genitals, anal and/or other regions before placing the absorbent article on the wearer. This procedure usually involves the caregiver applying the skin protective to their hands, and then wiping the same on the skin of the infant. To eliminate the need for this wasteful, messy, time-consuming, and easily forgotten procedure, there have been attempts to prepare absorbent articles which contain a protective or therapeutic skin care substance on the article's topsheet.

U.S. Pat. No. 3,585,998 to Hayford et al. teaches a disposable baby diaper, an interior liner of which carries an array of pressure-rupturable capsules containing baby oil. The patent teaches that it is desirable to break the capsules prior to using the diaper by applying pressure with such household items as a rolling pin, hand iron, etc. Articles disclosed by this patent have serious drawbacks. Namely, unless the capsules are ruptured by applying pressure prior to using the diaper or the bandage, the skin-care substance contained in the capsules is either not delivered at all or is delivered non-uniformly leaving some areas of skin uncoated.

U.S. Pat. No. 3,489,148 to Duncan et al. teaches a baby diaper comprising a hydrophobic and oleophobic topsheet wherein a portion of the topsheet is coated with a discontinuous film of oleaginous material. A major disadvantage of the diapers disclosed in the Duncan et al. reference is that the hydrophobic and oleophobic topsheets are slow in promoting transfer of urine to the underlying absorbent cores.

U.S. Pat. No. 5,643,588 to Roe et al. addresses some of the concerns presented by prior absorbent articles which were designed to deliver a skin protective material. In particular, Roe describes an absorbent article whose topsheet is surface treated with a lotion that comprises an emollient for facilitating easier cleaning of feces and other exudates and an agent which immobilizes the lotion so that it does not migrate from the point of initial application.

While the prior art describes articles designed to deliver compositions to provide skin care benefits, the prior art has failed to describe a regimen which results in maintained or improved skin health in regions of the wearer's body covered by absorbent articles, where the regimen does not require intervention from the caregiver in the form of manual application of skin care compositions. That is, the prior art has not recognized the importance of the repeated use of absorbent articles that automatically deliver sufficient levels of a composition to the wearer's skin that allows the maintenance or improvement of skin health in the region of the wearer covered by the absorbent article.

Accordingly, it would be desirable to provide a method: (1) wherein the condition of skin covered by the absorbent article is maintained in a natural, healthy condition or improved to a more healthy condition; and (2) that does not require intervention by the wearer or caregiver in the form of manual application of skin care agents.

Therefore, it is an object of the present invention to provide a method for maintaining or improving the skin health of an absorbent article wearer comprising repeated application of disposable absorbent articles that automatically deliver sufficient levels of a composition. In this regard, it is an object of the present invention to provide a method that comprises the application of absorbent articles which have a composition on a wearer-contacting surface, where the composition is transferable to the wearer's skin and is effective at maintaining or improving skin health.

These and other objects are obtained in accordance with the present invention, as will become readily apparent upon reading the following disclosure.

SUMMARY OF THE INVENTION

The present invention relates to a method for maintaining and/or improving skin health in the area of a wearer covered by an absorbent article. The absorbent article includes a vapor permeable backsheet, a liquid pervious topsheet positioned in facing relation with the backsheet, an absorbent core located between the backsheet and the topsheet. The absorbent article also includes skin care compositions thereon for maintaining and/or improving skin health. The method comprising the following steps:

(a) applying to the wearer an absorbent article having a skin care composition that provides a therapeutic and/or protective skin benefit upon transfer to the skin;

(b) transferring to the wearer at least a portion of the skin care composition during wear; and (c) repeating steps (a) and (b) with one or more additional articles with sufficient frequency to maintain or improve the health of the skin covered by the absorbent article relative to the skin covered by an equivalent absorbent article that does not comprise the skin care composition, and without the need for manual application of skin protective agents (e.g., by the caregiver or wearer).

DETAILED DESCRIPTION OF THE INVENTION

I. Definitions

Figure 1:
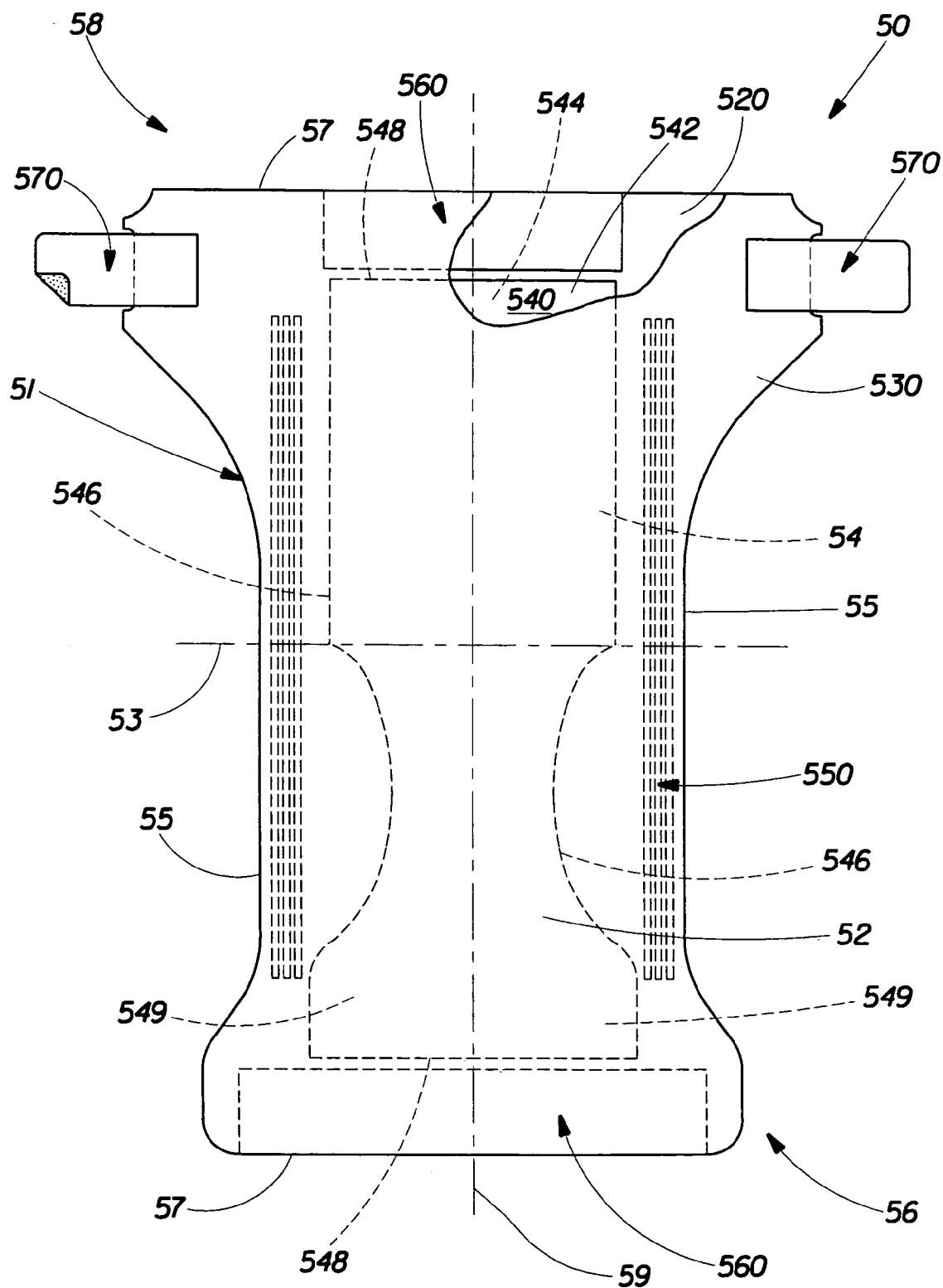
FIG. 1 is an absorbent article in the form of a diaper according to the present invention.

As used herein, the term "comprising" means that the various components, ingredients, or steps, can be conjointly employed in practicing the present invention. Accordingly, the term "comprising" encompasses the more restrictive terms "consisting essentially of" and "consisting of."

As used herein, the term "maintained" skin health means to preserve the natural state of healthy skin. The term "improved" skin health refers to a reduction in the extent of adverse skin effects. These terms describe skin health in the area covered by absorbent articles. It will be recognized that the methods of the present invention may both maintain and improve skin health in different regions of an individual wearer.

As used herein, the term "skin care composition" refers to any composition which comprises one or more agents which, when transferred from an article to a wearer's skin, provide a therapeutic and/or protective skin benefit. Representative materials are discussed in detail below.

As used herein, the term "treated article" means an absorbent article having a skin care composition on or migratable to at least one wearer-contacting surface of that article. An "equivalent article that does not comprise a skin care composition" is an article that is substantially the same as a treated article, in terms of topsheet, backsheet, absorbent core, chassis design, cuffs, etc., but which does not comprise a skin care composition that is transferred to the wearer during use.

As used herein, the term "wearer-contacting surface" of an absorbent article is one or more surfaces of any article components that contact the wearer at some time during the wear period. Wearer contacting surfaces include, but are not limited to, portions of the topsheet, leg cuffs, waist region, side panels, fastening tabs, etc., which contact a wearer during use.

Other terms are defined in the specification where initially discussed.

With respect to the skin care composition, all percentages, ratios and proportions used herein are by weight unless otherwise specified.

II. Methods for Maintaining and/or Improving Skin Health

As discussed, the adverse skin effects that result from the occlusive nature of current absorbent articles are well recognized. Efforts have been made to overcome these negative attributes by preparing articles that deliver beneficial compositions. However, Applicants are the first to recognize the benefit of a method comprising frequent cycles of cumulative delivery of a skin care composition to the wearer's skin to maintain or improve skin health. In this regard, the present invention relates to a method for maintaining or improving skin health in the area covered by an absorbent article, the method comprising the following steps:
(a) applying to the wearer an absorbent article having a skin care composition that provides a therapeutic and/or protective skin benefit upon transfer to the skin;
(b) transferring to the wearer at least a portion of the skin care composition during wear; and
(c) repeating steps (a) and (b) with one or more additional articles with sufficient frequency to maintain or improve the health of the skin covered by the absorbent article relative to the skin covered by an equivalent absorbent article that does not comprise the skin care composition, and without the need for manual application of skin protective agents (e.g., by the caregiver or wearer).

Applicants have discovered that, surprisingly, maintaining or improving health skin under absorbent articles can be accomplished coincidentally (or "automatically") with repeated use, over a period of time (e.g., several days), of absorbent articles that are treated with a composition that is transferred to the wearer under normal usage conditions (e.g., contact, movement, handling by the caregiver after application of the article, body heat, etc.). Thus, while previous attempts to address skin disorders associated with wearing absorbent articles have generally described steps (a) or (b) of the present method, none of those attempts appreciated the importance of step (c), corresponding to frequent cycles of cumulative delivery of a skin care composition to the wearer's skin to maintain or improve skin health. Applicants have further discovered that delivery of relatively low levels of the composition with each article wear are sufficient to obtain the skin benefits resulting from this novel method of cumulative composition delivery.

The article used in the present methods provides an available source from which the skin care composition transfers onto the skin continuously over time. As the composition is transferred, it accumulates on the skin surface to initiate and maintain its protective activity. As a used article is discarded and replaced by a new one, this cycle is repeated for further composition accumulation above and beyond what a single or original article would have delivered on its own. Certain of the ingredients for use in the composition are known to penetrate the stratum corneum (e.g., petrolatum, which is preferred for use herein). Thus, even as some amount of the composition is removed by cleaning, bathing, etc., or even if usage of treated articles as described herein is discontinued temporarily, some of the benefits of the skin composition will remain with the user. As usage of treated articles is resumed before all of the benefits of the composition have dissipated, the user will derive benefits, in terms of reduced erythema and/or rash, more rapidly than would a user who has not used treated articles.

As indicated above, it is generally recognized that skin under absorbent articles is more susceptible to degradation of that skin's condition. Typically, cutaneous manifestations of these skin conditions include redness (also referred to as erythema) and/or rash. As such, Applicants describe herein a method for maintaining or improving skin health in regions covered by an absorbent article, wherein the desired endpoint of the method is the reduction or avoidance of erythema and/or rash when compared to skin covered by an equivalent absorbent article that does not comprise the skin care composition.

Erythema and rash are the most common and well documented adverse medical conditions present on skin covered by absorbent articles. These conditions are readily assessed by expert skin graders. Hence the protocol for assessing the maintenance or improvement of skin health relies on assessment of rash and/or erythema. The protocol for assessing reduction or avoidance of rash and/or erythema provided by the methods of the present invention are described in detail in the Test Methods section below. In brief, the objective of the protocol is to determine whether use of a test article reduces the frequency and/or severity of skin rash and/or erythema in the diapered skin regions compared to an equivalent, untreated article. The test method involves comparisons of end point parameters between 2 groups of subjects who are assigned to wear the test or the control product for 3 consecutive weeks (a baseline week in which all subjects use the same control product is included prior to initiating the 3-week product comparison portion of the study). Per this approach, the skin in the diapered region of the users of the articles is examined twice per week at 3-4 day intervals by a clinical evaluator trained to evaluate diaper rash and erythema using a defined scale. At the completion of the study, the frequency and severity of diaper rash and erythema are compared between the test and control product groups using appropriate statistical procedures.

In one aspect, the improvement manifests itself as a statistically significant reduction in erythema and/or rash at a 90% confidence level, relative to skin covered an equivalent absorbent article that does not comprise the skin care composition. In this regard, it is preferable that the reduction or will manifest itself at a 95% confidence level.

Separately, it is recognized that one may observe large between-group differences (i.e., in the mean) in rash and/or erythema scores, yet due to large inter-subject variability fail to observe traditional statistically significant differences. In this regard, improvements of at least about 10% between group (control and test) means, though not necessarily statistical, may be recognized and appreciated by caregivers and users as providing skin care benefits. In this regard, the methods of the present invention will result in improvements in rash or erythema scores of at least about 10%, more preferably at least about 15%, still more preferably at least about 20%.

For purposes of the present disclosure, statistical or non-statistical improvements, defined above, in skin condition with regard to either erythema or rash at one or more wearer regions for the study group as a whole, or any gender or age or size subset of the study group, as described in the Test Method section, are considered to provide the desired skin benefits of the present invention. Preferably, the methods of the present invention will provide both erythema and rash benefits, at one or more wearer regions as described in the Test Method section.

III. Skin Care Composition

While the specific composition(s) delivered (referred to herein as "skin care composition" and "composition") in accordance with the present method is not the critical factor in achieving maintained skin condition of the area under absorbent articles, it is apparent that the composition must provide either a protective, nonocclusive function (e.g., a relatively liquid impervious but vapor pervious barrier) to avoid skin hyperhydration and skin exposure to materials contained in body exudates, or it must contain agents that deliver, either directly or indirectly, skin care benefits. For example, indirect benefits include improved removal of skin irritants such as feces or urine. The composition may be in a variety of forms, including, but not limited to, emulsions, lotions, creams, ointments, salves, powders, suspensions, encapsulations, gels, and the like.

As used herein, the term "effective amount of a skin care composition" refers to an amount of a particular composition which, when applied or migrated to one or more of the wearer-contacting surface(s) of an absorbent article(s), will be effective in providing a protective barrier and/or delivering a skin care benefit when delivered via absorbent articles over time. Of course, the effective amount of composition applied to the article will depend, to a large extent, on the particular composition used. Nonetheless, the quantity of the composition on at least a portion of the wearer-contacting surface of the absorbent article will preferably range from about 0.05 mg/in$^2$ (0.0078 mg/cm$^2$) to about 80 mg/in$^2$ (12 mg/cm$^2$), more preferably from about 1 mg/in$^2$ (0.16 mg/cm$^2$) to about 40 mg/in$^2$ (6 mg/cm$^2$), still more preferably from about 4 mg/in$^2$ (0.6 mg/cm$^2$) to about 26 mg/in$^2$ (4 mg/cm$^2$). These ranges are by way of illustration only and the skilled artisan will recognize that the nature of the composition will dictate the level that must be applied to achieve the desired skin benefits, and that such levels are ascertainable by routine experimentation in light of the present disclosure.

While the level of skin care composition applied to the absorbent article is an important aspect of the present methods, more important is the amount of composition transferred to the wearer's skin during use of one or more treated articles. Though the requisite level delivered to the skin to provide the desired skin benefits will depend to some degree on the nature of the composition employed, Applicants have found that relatively low levels may be delivered while still providing the desired skin effects. This is particularly true for preferred compositions, such as that described in Example 1.

Another benefit of the present method is the controlled application of the skin care composition to deliver the low but effective levels of composition required. This is in contrast to typically sporadic manual application of skin care agents, where the caregiver/user often applies significantly greater levels of material than are needed. Excessive materials added manually may adversely impact the fluid handling properties of the absorbent article, as a result of transfer from the skin to the article. Indeed, for certain materials, such as petrolatum, the levels applied manually may actually result in an occlusive effect, thereby compromising the skin. A benefit of the present methods is providing a barrier to surface moisture while avoiding occlusion of the skin (i.e., maintaining skin breathability). Thus, the present methods, which allow controlled composition delivery throughout the wear period, allow transfer of optimal levels of the composition to the skin to maintain and/or improve skin health.

The method for determining the amount of skin care composition transferred to a wearer's skin after wearing one or more treated articles is described in the Test Methods section below. With regard to the level of skin care composition that is transferred to the wearer during use of one treated absorbent article worn for a period of about 3 hours (a typical daytime wear time), particularly for preferred skin care compositions such as that described in Example 1, preferred is where at least about 0.01 mg/in$^2$ (0.0016 mg/cm$^2$), more preferably at least about 0.05 mg/in$^2$ (0.0078 mg/cm$^2$), still more preferably at least about 0.1 mg/in$^2$ (0.016 mg/cm$^2$), of the composition is transferred to the skin over a three hour wear period. Typically, the amount of composition delivered by one treated article will be from about 0.01 mg/in$^2$ (0.0016 mg/cm$^2$) to about 5 mg/in$^2$ (0.78 mg/cm$^2$), more preferably from about 0.05 mg/in$^2$ (0.0078 mg/cm$^2$) to about 3 mg/in$^2$ (0.47 mg/cm$^2$), still more preferably from about 0.1 mg/in$^2$ (0.016 mg/cm$^2$) to about 2 mg/in$^2$ (0.31 mg/cm$^2$), over a three hour wear period.

For continual use of treated articles (in other words, changes occur in accordance with normal use patterns, which typically include changes every 3 to 4 hours during the day and a fresh article before overnight sleep) such as for a period of 24 hours, it will be preferred that at least about 0.03 mg/in$^2$ (0.0047 mg/cm$^2$), more preferably at least about 0.1 mg/in$^2$ (0.016 mg/cm$^2$), still more preferably at least about 0.3 mg/in$^2$ (0.047 mg/cm$^2$), of the composition is transferred to the wearer's skin over the 24 hour period. Typically, the amount of composition delivered after a period of 24 hours where treated articles are applied at each change, will be from about 0.03 mg/in$^2$ (0.0047 mg/cm$^2$) to about 18 mg/in$^2$ (2.79 mg/cm$^2$), more typically from about 0.1 mg/in$^2$ (0.016 mg/cm$^2$) to about 10 mg/in$^2$ (1.55 mg/cm$^2$), still more typically from about 0.3 mg/in$^2$ (0.047 mg/cm$^2$) to about 6 mg/in$^2$ (0.93 mg/cm$^2$).

It will be recognized that of the numerous materials useful in the skin care compositions delivered to skin in accordance with the present methods, those that have been deemed safe and effective skin care agents are logical materials for use herein. Such materials include Category I actives as defined by the U.S. Federal Food and Drug Administration's (FDA) Tentative Final Monograph on Skin Protectant Drug Products for Over-the-Counter Human Use (21 C.F.R. § 347), which presently include: alantoin, aluminum hydroxide gel, calamine, cocoa butter, dimethicone, cod liver oil (in combination), glycerine, kaolin, petrolatum, lanolin, mineral oil, shark liver oil, white petrolatum, talc, topical starch, zinc acetate, zinc carbonate, zinc oxide, and the like. Other potentially useful materials are Category III actives as defined by the U.S. Federal Food and Drug Administration's Tentative Final Monograph on Skin Protectant Drug Products for Over-the-Counter Human Use (21 C.F.R. §347), which presently include: live yeast cell derivatives, aldioxa, aluminum acetate, microporous cellulose, cholecalciferol, colloidal oatmeal, cysteine hydrochloride, dexpanthenol, Peruvean balsam oil, protein hydrolysates, racemic methionine, sodium bicarbonate, Vitamin A, and the like.

Many of the FDA monographed skin care ingredients are currently utilized in commercially available skin care products, such as A and D® Ointment, Vaseline® Petroleum Jelly, Desitin® Diaper Rash Ointment and Daily Care®) ointment, Gold Bond® Medicated Baby Powder, Aquaphor® Healing Ointment, Baby Magic® Baby Lotion, Johnson's Ultra Sensitive® Baby Cream. These commercial products may be applied to absorbent articles to create treated articles for use in the present methods, either with or without modification of the product to facilitate delivery via this novel method.

As will be discussed hereinafter, the skin care compositions useful in the methods of the present invention preferably, though not necessarily, have a melting profile such that they are relatively immobile and localized on the wearer-contacting surface of the article at room temperature, are readily transferable to the wearer at body temperature, and yet are not completely liquid under extreme storage conditions. Preferably, the compositions are easily transferable to the skin by way of normal contact, wearer motion, and/or body heat. Because the composition preferably is substantially immobilized on the article's wearer-contacting surface, relatively low levels of composition are needed to impart the desired skin care benefits. In addition, special barrier or wrapping materials may be unnecessary in packaging the treated articles useful in the methods of the present invention.

In a preferred embodiment, the skin care compositions useful herein are solid, or more often semi-solid, at 20° C., i.e. at ambient temperatures. By "semisolid" is meant that the composition has a rheology typical of pseudoplastic or plastic liquids. When no shear is applied, the compositions can have the appearance of a semi-solid but can be made to flow as the shear rate is increased. This is due to the fact that, while the composition contains primarily solid components, it also includes some minor liquid components. Preferably, the compositions of the present invention have a zero shear viscosity between about $1.0 \times 10^6$ centipoise and about $1.0 \times 10^8$. More preferably, the zero shear viscosity is between about $5.0 \times 10^6$ centipoise and about $5.0 \times 10^7$ centipoise. As used herein the term "zero shear viscosity" refers to a viscosity measured at very low shear rates (e.g., 1.0 sec$^{-1}$) using plate and cone viscometer (a suitable instrument is available from TA Instruments of New Castle, Del. as model number CSL 100). One of skill in the art will recognize means other than high melting point components (as discussed below) can be used to provide comparable viscosities measured for such compositions comprising such means can be measured by extrapolating a plot of viscosity vs. shear rate for such compositions to a shear rate of zero at a temperature of about 20° C.

Preferred compositions are at least semi-solid at room temperature to minimize composition migration. In addition, the compositions preferably have a final melting point (100% liquid) above potential "stressful" storage conditions that can be greater than 45° C. (e.g., warehouse in Arizona, car trunk in Florida, etc.). Representative compositions having these melt characteristics are described in detail in U.S. Pat. No. 5,643,588 (Roe et al.), U.S. Pat. No. 5,607,760 (Roe et al.), U.S. Pat. No. 5,609,587, and U.S. Pat. No. 5,635,191, the disclosure of each of which is incorporated herein by reference. Specifically, preferred compositions will have the following melt profile:

| Characteristic | Preferred Range | Most Preferred |
| --- | --- | --- |
| % liquid at room temp. (20° C.) | 2-50 | 3-25 |
| % liquid at body temp. (37° C.) | 25-95 | 30-90 |
| final melting point (° C.) | ≧38 | ≧45 |

By being solid or semisolid at ambient temperatures, preferred compositions do not have a tendency to flow and migrate to a significant degree to undesired locations of the article to which they are applied. This means less skin care composition is required for imparting desirable therapeutic, protective and/or conditioning benefits.

To enhance immobility of preferred compositions, the viscosity of the formulated compositions should be as high as possible to prevent flow within the article to undesired location. Unfortunately, in some instances, higher viscosities may inhibit transfer of composition to the wearer's skin. Therefore, a balance should be achieved so the viscosities are high enough to keep the compositions localized on the surface of the article, but not so high as to impede transfer to the wearer's skin. Suitable viscosities for the compositions will typically range from about 5 to about 500 centipoise, preferably from about 5 to about 300 centipoise, more preferably from about 5 to about 100 centipoise, measured at 60° C. using a rotational viscometer (a suitable viscometer is available from Lab Line Instruments, Inc. of Melrose Park, Ill. as Model 4537). The viscometer is operated at 60 rpm using a number 2 spindle.

For compositions designed to provide a therapeutic and/or skin protective benefit, a useful active ingredient in these compositions is one or more skin protectants or emollients. As used herein, the term "emollient" is a material that protects against wetness or irritation, softens, soothes, supples, coats, lubricates, moisturizes, protects and/or cleanses the skin. (It will be recognized that several of the monographed actives listed above are "emollients", as that term is used herein.) In a preferred embodiment, these emollients will have either a plastic or liquid consistency at ambient temperatures, i.e., 20° C.

Representative emollients useful in the present invention include, but are not limited to, emollients that are petroleum-based; sucrose ester fatty acids; polyethylene glycol and derivatives thereof; humectants; fatty acid ester type; alkyl ethoxylate type; fatty acid ester ethoxylates; fatty alcohol type; polysiloxane type; propylene glycol and derivatives thereof; glycerine and derivatives thereof, including glyceride, acetoglycerides, and ethoxylated glycerides of $C_{12}$-$C_{28}$ fatty acids; triethylene glycol and derivatives thereof; spermaceti or other waxes; fatty acids; fatty alcohol ethers, particularly those having from 12 to 28 carbon atoms in their fatty chain, such as stearic acid; propoxylated fatty alcohols; other fatty esters of polyhydroxy alcohols; lanolin and its derivatives; kaolin and its derivatives; any of the monographed skin care agents listed above; or mixtures of these emollients. Suitable petroleum-based emollients include those hydrocarbons, or mixtures of hydrocarbons, having chain lengths of from 16 to 32 carbon atoms. Petroleum based hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons having from 16 to 20 carbon atoms. Petrolatum usually refers to more viscous mixtures of hydrocarbons having from 16 to 32 carbon atoms. Petrolatum and mineral oil are particularly preferred emollients for compositions of the present invention.

Suitable fatty acid ester type emollients include those derived from $C_{12}$-$C_{28}$ fatty acids, preferably $C_{16}$-$C_{22}$ saturated fatty acids, and short chain ($C_1$-$C_8$, preferably $C_1$-$C_3$) monohydric alcohols. Representative examples of such esters include methyl palmitate, methyl stearate, isopropyl laurate, isopropyl myristate, isopropyl palmitate, ethylhexyl palmitate and mixtures thereof. Suitable fatty acid ester emollients can also be derived from esters of longer chain fatty alcohols ($C_{12}$-$C_{28}$, preferably $C_{12}$-$C_{16}$) and shorter chain fatty acids e.g., lactic acid, such as lauryl lactate and cetyl lactate.

Suitable alkyl ethoxylate type emollients include $C_{12}$-$C_2$ fatty alcohol ethoxylates having an average degree of ethoxylation of from about 2 to about 30. Preferably, the fatty alcohol ethoxylate emollient is selected from the group consisting of lauryl, cetyl, and stearyl ethoxylates, and mixtures thereof, having an average degree of ethoxylation ranging from about 2 to about 23. Representative examples of such alkyl ethoxylates include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) and steareth-10 (a stearyl alcohol ethoxylate having an average degree of ethoxylation of 10). When employed, these alkyl ethoxylate emollients are typically used in combination with the petroleum-based emollients, such as petrolatum, at a weight ratio of alkyl ethoxylate emollient to petroleum-based emollient of from about 1:1 to about 1:5, preferably from about 1:2 to about 1:4.

Suitable fatty alcohol type emollients include $C_{12}$-$C_{22}$ fatty alcohols, preferably $C_{16}$-$C_{18}$ fatty alcohols. Representative examples include cetyl alcohol and stearyl alcohol, and mixtures thereof. When employed, these fatty alcohol emollients are typically used in combination with the petroleum-based emollients, such as petrolatum, at a weight ratio of fatty alcohol emollient to petroleum-based emollient of from about 1:1 to about 1:5, preferably from about 1:1 to about 1:2.

Other suitable types of emollients for use herein include polysiloxane compounds. In general, suitable polysiloxane materials for use in the present invention include those having monomeric siloxane units of the following structure:

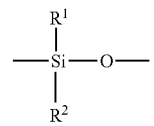

wherein, $R^1$ and $R^2$, for each independent siloxane monomeric unit can each independently be hydrogen or any alkyl, aryl, alkenyl, alkaryl, arakyl, cycloalkyl, halogenated hydrocarbon, or other radical. Any of such radicals can be substituted or unsubstituted. $R^1$ and $R^2$ radicals of any particular monomeric unit may differ from the corresponding functionalities of the next adjoining monomeric unit. Additionally, the polysiloxane can be either a straight chain, a branched chain or have a cyclic structure. The radicals $R^1$ and $R^2$ can additionally independently be other silaceous functionalities such as, but not limited to siloxanes, polysiloxanes, silanes, and polysilanes. The radicals $R^1$ and $R^2$ may contain any of a variety of organic functionalities including, for example, alcohol, carboxylic acid, phenyl, and amine functionalities.

Exemplary alkyl radicals are methyl, ethyl, propyl, butyl, pentyl, hexyl, octyl, decyl, octadecyl, and the like. Exemplary alkenyl radicals are vinyl, allyl, and the like. Exemplary aryl radicals are phenyl, diphenyl, naphthyl, and the like. Exemplary alkaryl radicals are toyl, xylyl, ethylphenyl, and the like. Exemplary aralkyl radicals are benzyl, alpha-phenylethyl, beta-phenylethyl, alpha-phenylbutyl, and the like. Exemplary cycloalkyl radicals are cyclobutyl, cyclopentyl, cyclohexyl, and the like. Exemplary halogenated hydrocarbon radicals are chloromethyl, bromoethyl, tetrafluorethyl, fluorethyl, trifluorethyl, trifluorotloyl, hexafluoroxylyl, and the like.

Viscosity of polysiloxanes useful may vary as widely as the viscosity of polysiloxanes in general vary, so long as the polysiloxane is flowable or can be made to be flowable for application to the absorbent article. This includes, but is not limited to, viscosity as low as 5 centistokes (at 37° C. as measured by a glass viscometer) to about 20,000,000 centistokes. Preferably the polysiloxanes have a viscosity at 37° C. ranging from about 5 to about 5,000 centistokes, more preferably from about 5 to about 2,000 centistokes, most preferably from about 100 to about 1000 centistokes. High viscosity polysiloxanes which themselves are resistant to flowing can be effectively deposited upon the absorbent articles by such methods as, for example, emulsifying the polysiloxane in surfactant or providing the polysiloxane in solution with the aid of a solvent, such as hexane, listed for exemplary purposes only. Particular methods for applying polysiloxane emollients to absorbent articles are discussed in more detail hereinafter.

Preferred polysiloxanes compounds for use in the present invention are disclosed in U.S. Pat. No. 5,059,282 (Ampulski et al), issued Oct. 22, 1991, which is incorporated herein by reference. Particularly preferred polysiloxane compounds for use as emollients in the compositions of the present invention include phenyl-functional polymethylsiloxane compounds (e.g., Dow Corning 556 Cosmetic-Grade Fluid: polyphenylmethylsiloxane) and cetyl or stearyl functionalized dimethicones such as Dow 2502 and Dow 2503 polysiloxane liquids, respectively. In addition to such substitution with phenyl-functional or alkyl groups, effective substitution may be made with amino, carboxyl, hydroxyl, ether, polyether, aldehyde, ketone, amide, ester, and thiol groups. Of these effective substituent groups, the family of groups comprising phenyl, amino, alkyl, carboxyl, and hydroxyl groups are more preferred than the others; and phenyl-functional groups are most preferred.

Suitable humectants include glycerine, propylene glycol, sorbitol, trihydroxy stearin, and the like.

When present, the amount of emollient that can be included in the composition will depend on a variety of factors, including the particular emollient involved, the skin benefits desired, the other components in the composition and like factors. The composition will comprise from 0 to about 100%, by total weight, of the emollient. Preferably, the composition will comprise from about 10 to about 95%, more preferably from about 20 to about 80%, and most preferably from about 40 to about 75%, by weight, of the emollient.

Another optional, preferred component of the therapeutic/skin protective compositions useful in the methods of the present invention is an agent capable of immobilizing the composition (including the preferred emollient and/or other skin condition/protective agents) in the desired location in or on the treated article. Because certain of the preferred emollients in the composition have a plastic or liquid consistency at 20° C., they tend to flow or migrate, even when subjected to modest shear. When applied to a wearer-contacting surface or other location of an absorbent article, especially in a melted or molten state, the emollient will not remain primarily in or on the treated region. Instead, the emollient will tend to migrate and flow to undesired regions of the article.

Specifically, if the emollient migrates into the interior of the article, it can cause undesired effects on the absorbency of the article core due to the hydrophobic characteristics of many of the emollients and other skin conditioning agents used in the compositions useful in the methods of the present invention. It also means that much more emollient has to be applied to the article to get the desired therapeutic and/or protective benefits. Increasing the level of emollient not only increases the cost, but also exacerbates the undesirable effect on the absorbency of the article's core and undesired transfer of composition during processing/converting of the treated articles.

The immobilizing agent counteracts this tendency of the emollient to migrate or flow by keeping the emollient primarily localized on the surface or in the region of the article to which the composition is applied. This is believed to be due, in part, to the fact that the immobilizing agent raises the melting point and/or viscosity of the composition above that of the emollient. Since the immobilizing agent is preferably miscible with the emollient (or solubilized in the emollient with the aid of an appropriate emulsifier), it entraps the emollient on the surface of the article's wearer contacting surface or in the region to which it is applied.

The immobilizing agent counteracts this tendency of the emollient to migrate or flow by keeping the emollient primarily localized on the surface or in the region of the article to which the composition is applied. This is believed to be due, in part, to the fact that the immobilizing agent raises the melting point and/or viscosity of the composition above that of the emollient. Since the immobilizing agent is preferably miscible with the emollient (or solubilized in the emollient with the aid of an appropriate emulsifier or dispersed therein), it entraps the emollient on the surface of the article's wearer contacting surface or in the region to which it is applied.

It is also advantageous to "lock" the immobilizing agent on the wearer contacting surface or the region of the article to which it is applied. This can be accomplished by using immobilizing agents which quickly set up (i.e., solidify) upon application to the article. In addition, outside cooling of the treated article via blowers, fans, cold rolls, etc. can speed up crystallization of the immobilizing agent.

In addition to being miscible with (or solubilized in) the emollient, the immobilizing agent will preferably have a melting profile that will provide a composition that is solid or semisolid at ambient temperature. In this regard, preferred immobilizing agents will have a melting point of at least about 35° C. This is so the immobilizing agent itself will not have a tendency to migrate or flow. Preferred immobilizing agents will have melting points of at least about 40° C. Typically, the immobilizing agent will have a melting point in the range of from about 50° to about 150° C.

When utilized, immobilizing agents useful herein can be selected from any of a number of agents, so long as the preferred properties of the skin care composition provide the skin benefits described herein. Preferred immobilizing agents will comprise a member selected from the group consisting of $C_{14}$-$C_{22}$ fatty alcohols, $C_{12}$-$C_{22}$ fatty acids, and $C_{12}$-$C_{22}$ fatty alcohol ethoxylates having an average degree of ethoxylation ranging from 2 to about 30, and mixtures thereof. Preferred immobilizing agents include $C_{16}$-$C_{18}$ fatty alcohols, most preferably crystalline high melting materials selected from the group consisting of cetyl alcohol, stearyl alcohol, behenyl alcohol, and mixtures thereof. (The linear structure of these materials can speed up solidification on the treated absorbent article.) Mixtures of cetyl alcohol and stearyl alcohol are particularly preferred. Other preferred immobilizing agents include $C_{16}$-$C_{18}$ fatty acids, most preferably selected from the group consisting of palmitic acid, stearic acid, and mixtures thereof. Mixtures of palmitic acid and stearic acid are particularly preferred. Still other preferred immobilizing agents include $C_{16}$-$C_{18}$ fatty alcohol ethoxylates having an average degree of ethoxylation ranging from about 5 to about 20. Preferably, the fatty alcohols, fatty acids and fatty alcohols are linear. Importantly, these preferred immobilizing agents such as the $C_{16}$-$C_{18}$ fatty alcohols increase the rate of crystallization of the composition causing the composition to crystallize rapidly onto the surface of the substrate.

Other types of immobilizing agents that may be used herein include polyhydroxy fatty acid esters, polyhydroxy fatty acid amides, and mixtures thereof. Preferred esters and amides will have three or more free hydroxy groups on the polyhydroxy moiety and are typically nonionic in character. Because of the possible skin sensitivity of those using articles to which the composition is applied, these esters and amides should also be relatively mild and non-irritating to the skin.

Suitable polyhydroxy fatty acid esters for use in the present invention will have the formula:

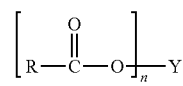

wherein R is a $C_5$-$C_{31}$ hydrocarbyl group, preferably straight chain $C_7$-$C_{19}$ alkyl or alkenyl, more preferably straight chain $C_9$-$C_{17}$ alkyl or alkenyl, most preferably straight chain $C_{11}$-$C_{17}$ alkyl or alkenyl, or mixture thereof; Y is a polyhydroxy-hydrocarbyl moiety having a hydrocarbyl chain with at least 2 free hydroxyls directly connected to the chain; and n is at least 1. Suitable Y groups can be derived from polyols such as glycerol, pentaerythritol; sugars such as raffinose, maltodextrose, galactose, sucrose, glucose, xylose, fructose, maltose, lactose, mannose and erythrose; sugar alcohols such as erythritol, xylitol, malitol, mannitol and sorbitol; and anhydrides of sugar alcohols such as sorbitan.

One class of suitable polyhydroxy fatty acid esters for use in the present invention comprises certain sorbitan esters, preferably the sorbitan esters of $C_{16}$-$C_{22}$ saturated fatty acids. Because of the manner in which they are typically manufactured, these sorbitan esters usually comprise mixtures of mono-, di-, tri-, etc. esters. Representative examples of suitable sorbitan esters include sorbitan palmitates (e.g., SPAN 40), sorbitan stearates (e.g., SPAN 60), and sorbitan behenates, that comprise one or more of the mono-, di- and tri-ester versions of these sorbitan esters, e.g., sorbitan mono-, di- and tri-palmitate, sorbitan mono-, di- and tri-stearate, sorbitan mono-, di and tri-behenate, as well as mixed tallow fatty acid sorbitan mono-, di- and tri-esters. Mixtures of different sorbitan esters can also be used, such as sorbitan palmitates with sorbitan stearates. Particularly preferred sorbitan esters are the sorbitan stearates, typically as a mixture of mono-, di- and tri-esters (plus some tetraester) such as SPAN 60, and sorbitan stearates sold under the trade name GLYCOMUL-S by Lonza, Inc. Although these sorbitan esters typically contain mixtures of mono-, di- and tri-esters, plus some tetraester, the mono- and di-esters are usually the predominant species in these mixtures.

Another class of suitable polyhydroxy fatty acid esters for use in the present invention comprises certain glyceryl monoesters, preferably glyceryl monoesters of $C_{16}$-$C_{22}$ saturated fatty acids such as glyceryl monostearate, glyceryl monopalmitate, and glyceryl monobehenate. Again, like the sorbitan esters, glyceryl monoester mixtures will typically contain some di- and triester. However, such mixtures should contain predominantly the glyceryl monoester species to be useful in the present invention.

Another class of suitable polyhydroxy fatty acid esters for use in the present invention comprise certain sucrose fatty acid esters, preferably the $C_{12}$-$C_{22}$ saturated fatty acid esters of sucrose. Sucrose monoesters and diesters are particularly preferred and include sucrose mono- and di-stearate and sucrose mono- and di- laurate.

Suitable polyhydroxy fatty acid amides for use in the present invention will have the formula:

wherein $R^1$ is H, $C_1$-$C_4$ hydrocarbyl, 2-hydroxyethyl, 2-hydroxypropyl, methoxyethyl, methoxypropyl or a mixture thereof, preferably $C_1$-$C_4$ alkyl, methoxyethyl or methoxypropyl, more preferably $C_1$ or $C_2$ alkyl or methoxypropyl, most preferably $C_1$ alkyl (i.e., methyl) or methoxypropyl; and $R^2$ is a $C_5$-$C_{31}$ hydrocarbyl group, preferably straight chain $C_7$-$C_{19}$ alkyl or alkenyl, more preferably straight chain $C_9$-$C_{17}$ alkyl or alkenyl, most preferably straight chain $C_{11}$-$C_{17}$ alkyl or alkenyl, or mixture thereof; and Z is a polyhydroxyhydrocarbyl moiety having a linear hydrocarbyl chain with at least 3 hydroxyls directly connected to the chain. See U.S. Pat. No. 5,174,927 (Honsa), issued Dec. 29, 1992 (herein incorporated by reference) which discloses these polyhydroxy fatty acid amides, as well as their preparation.

The Z moiety preferably will be derived from a reducing sugar in a reductive amination reaction; most preferably glycityl. Suitable reducing sugars include glucose, fructose, maltose, lactose, galactose, mannose, and xylose. High dextrose corn syrup, high fructose corn syrup, and high maltose corn syrup can be utilized, as well as the individual sugars listed above. These corn syrups can yield mixtures of sugar components for the Z moiety.

The Z moiety preferably will be selected from the group consisting of —$CH_2$—$(CHOH)_n$—$CH_2OH$, —$CH(CH_2OH)$—$[(CHOH)_{n-1}]$—$CH_2OH$, —$CH_2OH$—$CH_2$—$(CHOH)_2(CHOR^3)(CHOH)$—$CH_2OH$, where n is an integer from 3 to 5, and $R^3$ is H or a cyclic or aliphatic monosaccharide. Most preferred are the glycityls where n is 4, particularly —$CH_2$—$(CHOH)_4$—$CH_2OH$.

In the above formula, $R^1$ can be, for example, N-methyl, N-ethyl, N-propyl, N-isopropyl, N-butyl, N-2-hydroxyethyl, N-methoxypropyl or N-2-hydroxypropyl. $R^2$ can be selected to provide, for example, cocamides, stearamides, oleamides, lauramides, myristamides, capricamides, palmitamides, tallowamides, etc. The Z moiety can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

The most preferred polyhydroxy fatty acid amides have the general formula:

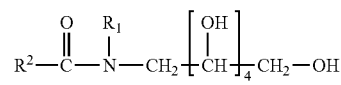

wherein $R^1$ is methyl or methoxypropyl; $R^2$ is a $C_{11}$-$C_{17}$ straight-chain alkyl or alkenyl group. These include N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl glucamide, N-tallowyl-N-methyl glucamide, or N-tallowyl-N-methoxypropyl glucamide.

As previously noted, some of the immobilizing agents may require an emulsifier for solubilization in the emollient. This is particularly the case for certain of the glucamides such as the N-alkyl-N-methoxypropyl glucamides having HLB values of at least about 7. Suitable emulsifiers will typically include those having HLB values below about 7. In this regard, the sorbitan esters previously described, such as the sorbitan stearates, having HLB values of about 4.9 or less have been found useful in solubilizing these glucamide immobilizing agents in petrolatum. Other suitable emulsifiers include steareth-2 (polyethylene glycol ethers of stearyl alcohol that conform to the formula $CH_3(CH_2)_{17}(OCH_2CH_2)_nOH$, where n has an average value of 2), sorbitan tristearate, isosorbide laurate, and glyceryl monostearate. The emulsifier can be included in an amount sufficient to solubilize the immobilizing agent in the emollient such that a substantially homogeneous mixture is obtained. For example, an approximately 1:1 mixture of N-cocoyl-N-methyl glucamide and petrolatum that will normally not melt into a single phase mixture, will melt into a single phase mixture upon the addition of 20% of a 1:1 mixture of Steareth-2 and sorbitan tristearate as the emulsifier.

Other types of ingredients that can be used as immobilizing agents, either alone, or in combination with the above-mentioned immobilizing agents, include waxes such as carnauba, ozokerite, beeswax, candelilla, paraffin, ceresin, esparto, ouricuri, rezowax, isoparaffin, and other known mined and mineral waxes. The high melt point of these materials can help immobilize the composition on the desired surface or location on the article. Addionally microcrystalline waxes are effective immobilizing agents. Microcrystalline waxes can aid in "locking" up low molecular weight hydrocarbons within the skin care composition. Preferably the wax is a paraffin wax. An example of a particularly preferred alternate immobilizing agent is a paraffin wax such as Parrafin S.P. 434 from Strahl and Pitsch Inc. P.O. Box 1098 West Babylon, N.Y. 11704.

The amount of the optional immobilizing agent that can be included in the composition will depend on a variety of factors, including the actives (e.g., emollients) involved, the particular immobilizing agent involved, if any, the other components in the composition, whether an emulsifier is required to solubilize the immobilizing agent in the other components, and like factors. When present, the composition will typically comprise from about 5 to about 90% of the immobilizing agent. Preferably, the composition will comprise from about 5 to about 50%, most preferably from about 10 to about 40%, of the immobilizing agent.

Of course, it is highly desirable that at least a portion of the article's topsheet be made of a hydrophilic material to promote rapid transfer of liquids (e.g., urine) through the topsheet. Similarly, it may be desirable that the composition be sufficiently wettable to ensure that liquids will transfer through the topsheet rapidly. Alternatively, hydrophobic skin care composition may be utilized, so long as they are applied such that the fluid handling properties of the topsheet are adequately maintained. (For example, as discussed below, nonuniform application of the composition to the topsheet is one means to accomplish this goal.) This diminishes the likelihood that body exudates will flow off the composition-treated topsheet rather than being drawn through the topsheet and being absorbed by the absorbent core. Where a hydrophilic composition is desired, depending upon the particular components used in the composition, a hydrophilic surfactant (or a mixture of hydrophilic surfactants) may, or may not, be required to improve wettability. For example, some immobilizing agents, such as N-cocoyl-N-methoxypropyl glucamide have HLB values of at least about 7 and are sufficiently wettable without the addition of hydrophilic surfactant. Other immobilizing agents such as the $C_{16}$-$C_{18}$ fatty alcohols having HLB values below about 7 may require addition of hydrophilic surfactant to improve wettability when the composition is applied to article topsheets. Similarly, a hydrophobic emollient such as petrolatum may require the addition of a hydrophilic surfactant if hydrophilic composition is desired. Of course, the concern around wettability is not a factor when the wearer-contacting surface under consideration is other than the article's topsheet or when fluid handling properties of the topsheet are adequately maintained via other means (e.g., nonuniform application).

Suitable hydrophilic surfactants will preferably be miscible with the other components of the skin care composition so as to form blended mixtures. Because of possible skin sensitivity of those using disposable absorbent products to which the composition is applied, these surfactants should also be relatively mild and non-irritating to the skin. Typically, these hydrophilic surfactants are nonionic to be not only non-irritating to the skin, but also to avoid other undesirable effects on any other structures within the treated article. For example, reductions tissue laminate tensile strength, adhesive bond sufficiencies, and the like.

Suitable nonionic surfactants may be substantially nonmigratory after the composition is applied to the articles and will typically have HLB values in the range of from about 4 to about 20, preferably from about 7 to about 20. To be nonmigratory, these nonionic surfactants will typically have melt temperatures greater than the temperatures commonly encountered during storage, shipping, merchandising, and use of disposable absorbent products, e.g., at least about 30° C. In this regard, these nonionic surfactants will preferably have melting points similar to those of the immobilizing agents previously described.

Suitable nonionic surfactants for use in compositions that will be applied to the articles, at least in the liquid discharge region of the diaper, include alkylglycosides; alkylglycoside ethers as described in U.S. Pat. No. 4,011,389 (Langdon, et al), issued Mar. 8, 1977, which is incorporated by reference; alkylpolyethoxylated esters such as Pegosperse 1000MS (available from Lonza, Inc., Fair Lawn, N.J.), ethoxylated sorbitan mono-, di- and/or tri-esters of $C_{12}$-$C_{18}$ fatty acids having an average degree of ethoxylation of from about 2 to about 20, preferably from about 2 to about 10, such as TWEEN 60 (sorbitan esters of stearic acid having an average degree of ethoxylation of about 20) and TWEEN 61 (sorbitan esters of stearic acid having an average degree of ethoxylation of about 4), and the condensation products of aliphatic alcohols with from about 1 to about 54 moles of ethylene oxide. The alkyl chain of the aliphatic alcohol is typically in a straight chain (linear) configuration and contains from about 8 to about 22 carbon atoms. Particularly preferred are the condensation products of alcohols having an alkyl group containing from about 11 to about 22 carbon atoms with from about 2 to about 30 moles of ethylene oxide per mole of alcohol. Examples of such ethoxylated alcohols include the condensation products of myristyl alcohol with 7 moles of ethylene oxide per mole of alcohol, the condensation products of coconut alcohol (a mixture of fatty alcohols having alkyl chains varying in length from 10 to 14 carbon atoms) with about 6 moles of ethylene oxide. A number of suitable ethoxylated alcohols are commercially available, including TERGITOL 15-S-9 (the condensation product of $C_{11}$-$C_{15}$ linear alcohols with 9 moles of ethylene oxide), marketed by Union Carbide Corporation; KYRO EOB (condensation product of $C_{13}$-$C_{15}$ linear alcohols with 9 moles of ethylene oxide), marketed by The Procter & Gamble Co., the NEODOL brand name surfactants marketed by Shell Chemical Co., in particular NEODOL 25-12 (condensation product of $C_{12}$-$C_{15}$ linear alcohols with 12 moles of ethylene oxide) and NEODOL 23-6.5T (condensation product of $C_{12}$-$C_{13}$ linear alcohols with 6.5 moles of ethylene oxide that has been distilled (topped) to remove certain impurities), and especially the PLURAFAC brand name surfactants marketed by BASF Corp., in particular PLURAFAC A-38 (a condensation product of a $C_{18}$ straight chain alcohol with 27 moles of ethylene oxide). (Certain of the hydrophilic surfactants, in particular ethoxylated alcohols such as NEODOL 25-12, can also function as alkyl ethoxylate emollients). Other examples of preferred ethoxylated alcohol surfactants include ICI's class of Brij surfactants and mixtures thereof, with Brij 72 (i.e., Steareth-2) and Brij 76 (i.e., Steareth-10) being especially preferred. Also, mixtures of cetyl alcohol and stearyl alcohol ethoxylated to an average degree of ethoxylation of from about 10 to about 20 may also be used as the hydrophilic surfactant.

Another type of suitable surfactant for use in the composition includes Aerosol OT, a dioctyl ester of sodium sulfosuccinic acid marketed by American Cyanamid Company.

Still another type of suitable surfactant for use in the composition includes silicone copolymers such as General Electric SF 1188 (a copolymer of a polydimethylsiloxane and a polyoxyalkylene ether) and General Electric SF 1228 (a silicone polyether copolymer). These silicone surfactants can be used in combination with the other types of hydrophilic surfactants discussed above, such as the ethoxylated alcohols.

These silicone surfactants have been found to be effective at concentrations as low as 0.1%, more preferably from about 0.25 to about 1.0%, by weight of the composition.

Where a hydrophilic composition is desired, the amount of hydrophilic surfactant required to increase the wettability of the composition to a desired level will depend in-part upon the HLB value and level of immobilizing agent, if any, used, the HLB value of the surfactant used and like factors. The composition can comprise from about 0.1 to about 50% of the hydrophilic surfactant when needed to increase the wettability properties of the composition. Preferably, the composition comprises from about 1 to about 25%, most preferably from about 10 to about 20%, of the hydrophilic surfactant when needed to increase wettability.

Compositions can comprise other components typically present in emulsions, creams, ointment, lotions, powders, suspensions, etc. of this type. These components include water, viscosity modifiers, perfumes, disinfectant antibacterial actives, antiviral agents, vitamins, pharmaceutical actives, film formers, deodorants, opacifiers, astringents, solvents, preservatives, and the like. In addition, stabilizers can be added to enhance the shelf life of the composition such as cellulose derivatives, proteins and lecithin. All of these materials are well known in the art as additives for such formulations and can be employed in appropriate amounts in the compositions for use herein.

If water-based skin care compositions are used, a preservative will be needed. Suitable preservatives include propyl paraben, methyl paraben, benzyl alcohol, benzylkonnium, tribasic calcium phosphate, BHT, or acids such as citric, tartaric, maleic, lactic, malic, benzoic, salicylic, and the like. Suitable viscosity increasing agents include some of the agents described as effective immobilizing agents. Other suitable viscosity increasing agents include alkyl galactomannan, silica, talc, magnesium silicate, sorbitol, colloidal silicone dioxide, magnesium aluminum silicate, zinc stearate, wool wax alcohol, sorbiton, sesquioleate, cetyl hydroxy ethyl cellulose and other modified celluloses. Suitable solvents include propylene glycol, glycerine, cyclomethicone, polyethylene glycols, hexalene glycol, diol and multi-hydroxy based solvents. Suitable vitamins include A, D-3, E, B-5 and E acetate.

IV. Absorbent Articles

As used herein, the term "absorbent article" refers to a device which absorbs and retains body exudates. The term "disposable" is used herein to describe absorbent articles which are not intended to be laundered or otherwise restored or reused as an absorbent article after a single use. Examples of disposable absorbent articles include feminine hygiene garments such as sanitary napkins, panty-liners and tampons, diapers, incontinence briefs, diaper holders, training pants, and the like.

Disposable absorbent articles typically comprise a liquid pervious topsheet, a liquid impervious backsheet and an absorbent core positioned between the topsheet and the backsheet. Disposable absorbent articles and components thereof, including the topsheet, backsheet, absorbent core, and any individual layers of these components, have a body facing surface and a garment facing surface. As used herein, "body facing surface" means that surface of the article or component which is intended to be worn toward or adjacent to the body of the wearer, while the "garment facing surface" is on the opposite side and is intended to be worn toward or placed adjacent to the wearers clothing or undergarments when the disposable absorbent article is worn.

The following description generally discusses the absorbent core, topsheet, and backsheet materials that are useful in disposable absorbent articles that are used in the methods of the present invention. It is to be understood that this general description applies to these components of the specific absorbent articles shown in FIG. 1 and further described below, in addition to those of other disposable absorbent articles which are generally described herein.

In general, the absorbent core is capable of absorbing or retaining liquids (e.g., menses, urine, and/or other body exudates). The absorbent core is preferably compressible, conformable, and non-irritating to the wearer's skin. The absorbent core may be manufactured in a wide variety of sizes and shapes (e.g., rectangular, oval, hourglass, "T" shaped, dog bone, asymmetric, etc.). In addition to the absorbent composites of the present invention, the absorbent core may include any of a wide variety of liquid-absorbent materials commonly used in absorbent articles, such as comminuted wood pulp, which is generally referred to as airfelt. Examples of other suitable absorbent materials for use in the absorbent core include creped cellulose wadding; meltblown polymers including coform; chemically stiffened, modified or crosslinked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core may also be varied (e.g., the absorbent core may have varying caliper zones and/or have a profile so as to be thicker in the center; hydrophilic gradients; gradients of the absorbent composite of the present invention, superabsorbent gradients; or lower average density and lower average basis weight zones, e.g., acquisition zones; or may comprise one or more layers or structures). The total absorbent capacity of the absorbent core should, however, be compatible with the design loading and the intended use of the absorbent article. Further, the size and absorbent capacity of the absorbent core may be varied to accommodate different uses such as diapers, incontinence pads, pantiliners, regular sanitary napkins, and overnight sanitary napkins, and to accommodate wearers ranging from infants to adults.

The absorbent core can include other absorbent components that are often used in absorbent articles, for example, a dusting layer, a wicking or acquisition layer, or a secondary topsheet for increasing the wearer's comfort.

The topsheet is preferably compliant, soft feeling, and non-irritating to the wearer's skin. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers), including apertured nonwovens; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, spunlace carded, wet-laid, melt-blown, hydroentangled, hydroformed, hydroapertured, combinations of the above, or the like.

The backsheet is impervious to liquids (e.g., menses and/or urine) and is preferably comprises a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, or composite materials such as a film-coated nonwoven material.

The backing materials or outer covers of diapers have traditionally been made from plastic films due to cost considerations and the liquid impermeable nature of plastic films. While plastic films are efficient at containing liquids and other waste matters during use, the same plastic films have certain disadvantages in that they are not pleasing to the touch and they do not readily pass water vapor so that, from a wearer wellness standpoint, plastic films tend to cause skin hydration thereby making infants more prone to diaper rash. One solution has been to supplant normal nonporous plastic films with breathable plastic films as the diaper backing materials. For the purposes of the present invention, a film is "breathable" if it has a water vapor transmission rate of at least 100 $g/m^2/24$ hours as calculated using the test method outlined below with respect to the examples. Polyolefin films are often used for making breathable films. A particularly useful film for such application is made from a linear polyolefin containing organic and/or inorganic fillers. Such filled polyolefin films provide good water vapor transmission thereby making the diapers more comfortable to the wearer. As a result, the relative humidity and temperature within the diaper or other product can be reduced by using breathable materials. Despite this, such breathable films have the disadvantage of being cold and clammy because breathable films pass moisture to the outside of the product where it condenses readily on the film surface. Consequently, another solution has been to attempt to use nonwoven materials as the backing material for diapers. Fibrous nonwoven webs when used as the backing material for diapers alleviate the above-mentioned film problems, however, such fibrous nonwoven webs generally provide poor barriers to the passage of liquids including urine. In view of the foregoing deficiencies of both films and fibrous nonwovens, attempts have been made to combine the two materials thereby making it possible to rely upon the strengths of one material to overcome the weaknesses of the other.

A suitable backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-1401 and by Tredegar Film Products of Terre Haute, Ind., under the designation XP-39385. The backsheet is preferably embossed and/or matte finished to provide a more clothlike appearance. The size of the backsheet is dictated by the size of the absorbent core and the exact absorbent article design selected.

As discussed above, while it is preferred that the composition which is continually, automatically transferred to the wearer's skin by wearing articles described herein be relatively impervious to liquids such as urine and runny feces, it is also preferred that the composition be relatively vapor pervious to provide a nonocclusive barrier for the skin. In this regard, to further facilitate the maintenance or improvement of skin health, uncompromised skin in the wearer's region under the absorbent article via the presently disclosed methods, preferred absorbent articles useful in those methods are those which also provide "breathability", to facilitate relatively lower relative humidity in the area between the skin and the absorbent article. Recently, attempts have been disclosed that are directed to improving wearer skin condition by allowing the overhydrated skin to dehydrate to an acceptable level by allowing either air to reach the skin (thus minimizing potential occlusion effects) and/or providing means for removing water vapor from the surface of the skin. Generally, such mechanisms are referred to as "breathability" or "vapor or moisture permeability". Specific examples include feminine hygiene products, such as catamenial products or so-called pantiliners as described in EP-A-0.104.906; EP-A-0.171.041; EP-A-0.710.471; the disclosure of each of which is incorporated herein by reference. Such products generally have relatively low liquid storage capacity when compared, for example, to baby diapers or adult incontinence products, which have theoretical storage capacities more than ten times the capacity of a feminine hygiene product. The "breathable" articles described in these references may be treated with skin care composition as described herein, and such treated articles may be useful in the methods of the present invention.

Such breathable materials can be various kinds of webs, such as films which are rendered air/vapor pervious by aperturing as described in U.S. Pat. No. 5,628,737, which issued in the name of Dobrin, et al. on May 13, 1997, or by exploiting the "microporosity" property as described in EP-A-0.238.200; EP-A-0.288.021; EP-A-0.352.802; EP-A-0.515.501; U.S. Pat. No. 4,713,068, whereby small voids are created within the film similar to very small cracks. WO 94/23107; WO 94/28224; U.S. Pat. No. 4,758,339 which issued in the name of Yeo, et al. on Jul. 19, 1988; and EP-A-0.315.013 all describe alternative breathable materials which can be fibrous textile or non-woven webs, with air/vapor easily penetrating through the relatively large pores of the structure. Such webs, being either treated or untreated with regard to improving their liquid impermeability properties, such as described in EP-A-0.196.654. In WO 95/16562 a laminate of a non-woven with a breathable film is disclosed. Further disclosures such as in WO 95/16746 relate to other materials allowing water molecules to diffuse through. Also, combinations of various materials comprising various layers of any of the above elements are also well known. Absorbent articles using any of the approaches described in these references (each of which is incorporated herein by reference) in combination with delivering a composition as described herein may be used to carry out the methods of the present invention. Indeed, a particularly preferred absorbent article for use in the present methods is described in detail in U.S. Pat. No. 6,107,537, issued to Elder et al. on Aug. 22, 2000, the disclosure of which is incorporated herein by reference.

The backsheet and the topsheet are positioned adjacent the garment facing surface and the body facing surface, respectively, of the absorbent core. The absorbent core is preferably joined with the topsheet, the backsheet, or both in any manner as is known by attachment means (not shown in FIG. 1) such as those well known in the art. However, embodiments of the present invention are envisioned wherein portions or the entire absorbent core are unattached to either the topsheet, the backsheet, or both.

For example, the backsheet and/or the topsheet may be secured to the absorbent core or to each other by a uniform continuous layer of adhesive, a patterned layer of adhesive, or an array of separate lines, spirals, or spots of adhesive. Adhesives which have been found to be satisfactory are manufactured by H.B. Fuller Company of St. Paul, Minn. under the designation HL-1258 or H-2031. The attachment means will preferably comprise an open pattern network of filaments of adhesive as is disclosed in U.S. Pat. No. 4,573,986, issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zwieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

A preferred disposable absorbent article in which the wearer contacting surface is treated with a composition are diapers. As used herein, the term "diaper" refers to an absorbent article generally worn by infants, and incontinent persons, that is worn about the lower torso of the wearer. In other words, the term "diaper" includes infant diapers, training pants, adult incontinence devices, etc.

FIG. 1 is a plan view of the diaper 50 useful in the methods of the present invention in its flat-out, uncontracted state (i.e., with elastic induced contraction pulled out) with portions of the structure being cut-away to more clearly show the construction of the diaper 50 and with the portion of the diaper 50 which faces away from the wearer (the outer surface) oriented towards the viewer. As shown in FIG. 1, the diaper 50 preferably comprises a liquid pervious topsheet 520; a liquid impervious backsheet 530 joined with the topsheet 520; an absorbent core 540 positioned between the topsheet 520 and the backsheet 530, the absorbent core 540 having a garment facing surface 542, a body facing surface 544, side edges 546, waist edges 548, and ears 549. The diaper 50 preferably further comprises elasticized leg cuffs 550; an elastic waist feature multiply designated as 560; and a fastening system generally multiply designated as 570.

The diaper 50 is shown in FIG. 1 to have an outer surface 52, an inner surface 54 corresponding to the body facing surface which is opposed to the outer surface 52, a first waist region 56, a second waist region 58, and a periphery 51 which is defined by the outer edges of the diaper 50 in which the longitudinal edges are designated 55 and the end edges are designated 57. (While the skilled artisan will recognize that a diaper is usually described in terms of having a pair of waist regions and a crotch region between the waist regions, in this application, for simplicity of terminology, the diaper 50 is described as having only waist regions including a portion of the diaper which would typically be designated as part of the crotch region). The body facing surface 54 of the diaper 50 comprises that portion of the diaper 50 which is positioned adjacent to the wearer's body during use. The body facing surface 54 generally is formed by at least a portion of the topsheet 520 and other components that may be joined to the topsheet 520, such as leg cuffs 550, as well as any regions to which the topsheet may not extend but which still contact the wearer, such as the waist feature 560, side panels and the like. The outer surface 52 comprises that portion of the diaper 50 which is positioned away from the wearer's body (i.e., the outer surface 52 generally is formed by at least a portion of the backsheet 530 and other components that may be joined to the backsheet 530). The first waist region 56 and the second waist region 58 extend, respectively, from the end edges 57 of the periphery 51 to the lateral centerline 53 of the diaper 50. FIG. 1 also shows the longitudinal centerline 59.

FIG. 1 shows a preferred embodiment of the diaper 50 in which the topsheet 520 and the backsheet 530 have length and width dimensions generally larger than those of the absorbent core 540. The elasticized leg cuffs 550 and the backsheet 530 extend beyond the edges of the absorbent core 540 to thereby form the periphery 51 of the diaper 50.

Diapers of the present invention can have a number of well known configurations, with the absorbent cores thereof being adapted to the present invention. Exemplary configurations are described generally in U.S. Pat. No. 3,860,003 issued to Buell on Jan. 14, 1975; U.S. Pat. No. 5,151,092 issued to Buell et al. on Sep. 29, 1992; U.S. Pat. No. 5,221,274 issued to Buell et al. on Jun. 22, 1993. Each of these patents is incorporated herein by reference. Another diaper configuration to which the present invention can be readily adapted are described in co-pending U.S. patent application Ser. Nos. 08/203,456; filed on Feb. 28, 1994 and incorporated herein by reference. The absorbent cores of diapers described in these patents can be adapted in light of the teachings herein to include the absorbent composite of the present invention as an absorbent gelling material described therein.

A topsheet 520 which is particularly suitable for use in the diaper 50, is carded and thermally bonded by means well known to those skilled in the fabrics art. A satisfactory topsheet for the present invention comprises staple length polypropylene fibers having a denier of about 2.2 As used herein, the term "staple length fibers" refers to those fibers having a length of at least about 15.9 mm (0.625 inches). Preferably, the topsheet has a basis weight from about 14 to about 25 grams per square meter. A suitable topsheet is manufactured by Veratec, Inc., a Division of International Paper Company, of Walpole, Mass. under the designation P-8.

The topsheet 520 of diaper 50 is preferably made of a hydrophilic material to promote rapid transfer of liquids (e.g., urine) through the topsheet. If the topsheet is made of a hydrophobic material, at least portions of the upper surface of the topsheet are treated to be hydrophilic so that liquids will transfer through the topsheet more rapidly. This diminishes the likelihood that body exudates will flow off the topsheet rather than being drawn through the topsheet and being absorbed by the absorbent core. The topsheet can be rendered hydrophilic by treating it with a surfactant. Suitable methods for treating the topsheet with a surfactant include spraying the topsheet material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein.

Alternatively, the topsheet may be in the form of an apertured formed film, which is preferred in feminine hygiene absorbent articles. Apertured formed films are useful because they are pervious to body liquids and yet non-absorbent and have a reduced tendency to allow liquids to pass back through and rewet the wearer's skin. Thus, the surface of the formed film that is in contact with the body remains dry, thereby reducing body soiling and creating a more comfortable feel for the wearer. Suitable formed films are described in U.S. Pat. No. 3,929,135 (Thompson), issued Dec. 30, 1975; U.S. Pat. No. 4,324,246 (Mullane et al.), issued Apr. 13, 1982; U.S. Pat. No. 4,342,314 (Radel. et al.), issued Aug. 3, 1982; U.S. Pat. No. 4,463,045 (Ahr et al.), issued Jul. 31, 1984; and U.S. Pat. No. 5,006,394 (Baird), issued Apr. 9, 1991. Each of these patents are incorporated herein by reference. Particularly preferred microapertured formed film topsheets are disclosed in U.S. Pat. No. 4,609,518 (Curro et al), issue Sep. 2, 1986 and U.S. Pat. No. 4,629,643 (Curro et al), issued Dec. 16, 1986, which are incorporated by reference. The preferred topsheet for use in feminine hygiene products is the formed film described in one or more of the above patents and marketed on sanitary napkins by The Procter & Gamble Company of Cincinnati, Ohio as "DRI-WEAVE®."

The body facing surface of the formed film topsheet can be hydrophilic so as to help body liquids to transfer through the topsheet faster than if the body surface was not hydrophilic so as to diminish the likelihood that liquid will flow off the topsheet rather than flowing into and being absorbed by the absorbent structure. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated by reference. Alternatively, the body facing surface of the topsheet can be made hydrophilic by treating it with a surfactant such as is described in the above referenced U.S. Pat. No. 4,950,254, incorporated herein by reference.

In a preferred embodiment of a diaper as described herein, the backsheet 530 has a modified hourglass shape extending beyond the absorbent core a minimum distance of about 1.3 cm to about 6.4 cm (about 0.5 to about 2.5 inch) around the entire diaper periphery.

The absorbent core 540 may take on any size or shape that is compatible with the diaper 50. One preferred embodiment of the diaper 50 has an asymmetric, modified T-shaped absorbent core 540 having ears in the first waist region but a generally rectangular shape in the second waist region. Exemplary absorbent materials for use as the absorbent core of articles useful in the present methods are described, e.g., in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

In a preferred embodiment, the diaper 50 further comprises elasticized leg cuffs 550 for providing improved containment of liquids and other body exudates; an elastic waist feature 560 that provides improved fit and containment; and a fastening system 570 which forms a side closure which maintains the first waist region 56 and the second waist region 58 in an overlapping configuration such that lateral tensions are maintained around the circumference of the diaper to maintain the diaper on the wearer. The diaper 50 may also comprise elasticized waist bands (not shown) and/or elasticized side panels (also not shown) in the waist regions 56 and 58 to provide an elastically extensible feature that provides a more comfortable and contouring fit and more effective application of the diaper 50.

The elasticized leg cuffs 550 can be constructed in a number of different configurations, including those described in U.S. Pat. No. 3,860,003; U.S. Pat. No. 4,909,803, issued to Aziz et al. on Mar. 20, 1990; U.S. Pat. No. 4,695,278, issued to Lawson on Sep. 22, 1987; and U.S. Pat. No. 4,795,454, issued to Dragoo on Jan. 3, 1989, each being incorporated herein by reference. Absorbent articles having elasticized cuffs that are treated with a composition that may be useful herein are disclosed in U.S. Pat. No. 6,156,024, issued to Schulte et al. on Dec. 5, 2000, and U.S. Patent application Ser. No. 08/840,039 (now abandoned), both of which are incorporated by reference.

The elasticized waist feature preferably comprises an elasticized waistband (not shown) that may be constructed in a number of different configurations including those described in U.S. Pat. No. 4,515,595 issued to Kievit et al. on May 7, 1985; U.S. Pat. No. 5,026,364 issued to Robertson on Jun. 25, 1991; and the above referenced U.S. Pat. No. 5,151,092 issued to Buell et al. on Sep. 29, 1992, each of these references being incorporated herein by reference.

The elasticized side panels may be constructed in a number of configurations. Examples of diapers with elasticized side panels positioned in the ears (ear flaps) of the diaper are disclosed in U.S. Pat. No. 4,857,067, issued to Wood, et al. on Aug. 15, 1989; U.S. Pat. No. 4,381,781, issued to Sciaraffa, et al. on May 3, 1983; U.S. Pat. No. 4,938,753, issued to Van Gompel, et al. on Jul. 3, 1990; and U.S. Pat. No. 5,151,092, issued to Buell et al. on Sep. 29, 1992; each of which are incorporated herein by reference.

Exemplary fastening systems 570 are disclosed in U.S. Pat. No. 4,846,815, issued to Scripps on Jul. 11, 1989; U.S. Pat. No. 4,894,060, issued to Nestegard on Jan. 16, 1990; U.S. Pat. No. 4,946,527, issued to Battrell on Aug. 7, 1990; U.S. Pat. No. 3,848,594, issued to Buell on Nov. 19, 1974; U.S. Pat. No. BI 4,662,875, issued to Hirotsu et al. on May 5, 1987; and U.S. Pat. No. 5,151,092, issued to Buell et al. on Sep. 29, 1992; each of which is incorporated herein by reference.

The diaper 50 is preferably applied to a wearer by positioning one of the waist regions of the diaper, preferably the second waist region 58, under the wearer's back and drawing the remainder of the diaper between the wearer's legs so that the other waist region, preferably the first waist region 56, is positioned across the front of the wearer. The fastening system is then applied to effect a side closure.

Of course, it will be recognized that any absorbent article design may be utilized to carry out the methods of the present invention, so long as skin care composition is applied to the article so as to be transferred to the skin during use. The disclosure above is merely for illustrative purposes.

The methods of the present invention may also employ training pants to effect delivery of the desired skin care composition. The term "training pants", as used herein, refers to disposable garments having fixed sides and leg openings designed for infant or adults wearers. Training pants (also referred in the art as "pull on" products) are placed in position on the wearer by inserting the wearer's legs into the leg openings and sliding the training pant into position about the wearer's lower torso. Suitable training pants are disclosed in U.S. Pat. No. 5,246,433, issued to Hasse, et al. on Sep. 21, 1993, U.S. Pat. No. 5,569,234, issued to Buell et al. on Oct. 29, 1996, U.S. Pat. No. 4,940,464, issued to Van Gompel et al. on Jul. 10, 1990 and U.S. Pat. No. 5,092,861, issued to Nomura et al. on Mar. 3, 1992, the disclosure of each of which is incorporated herein by reference.

Another disposable absorbent article for use in the present methods are incontinence articles. The term "incontinence article" refers to pads, undergarments (pads held in place by a suspension system of same type, such as a belt, or the like), inserts for absorbent articles, capacity boosters for absorbent articles, briefs, bed pads, and the like regardless of whether they are worn by adults or other incontinent persons. Suitable incontinence articles are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and in U.S. patent application Ser. No. 07/637,090 filed by Noel, et al. on Jan. 3, 1991 (PCT Publication No. WO 92/11830 published on Jul. 23, 1992). The disclosure of each of these references is incorporated herein.

Another disposable absorbent article for use in the present methods are feminine hygiene articles, such as sanitary napkins. Suitable feminine hygiene articles are disclosed in U.S. Pat. No. 4,556,146, issued to Swanson et al. on Dec. 3, 1985, U.S. Pat. No. B14,589,876, issued to Van Tilberg on Apr. 27, 1993, U.S. Pat. No. 4,687,478, issued to Van Tilburg on Aug. 18, 1997, U.S. Pat. No. 4,950,264, issued to Osborn, III on Aug. 21, 1990, U.S. Pat. No. 5,009,653, issued to Osborn, III on Apr. 23, 1991, U.S. Pat. No. 5,267,992, issued to Van Tilburg on Dec. 7, 1993, U.S. Pat. No. 5,389,094, issued to Lavash et al. on Feb. 14, 1995, U.S. Pat. No. 5,413,568, issued to Roach et al. on May 9, 1995, U.S. Pat. No. 5,460,623, issued to Emenaker et al. on Oct. 24, 1995, U.S. Pat. No. 5,489,283, issued Van Tilburg on Feb. 6, 1996, U.S. Pat. No. 5,569,231, issued to Emenaker et al. on Oct. 29, 1996, and U.S. Pat. No. 5,620,430, issued to Bamber on Apr. 15, 1997, the disclosure of each of which is incorporated by reference herein.

V. Treating Articles with Composition

In preparing absorbent articles to carry out the methods of the present invention, the skin care composition is applied such that during wear, at least some portion of the composition will transfer from the treated article to the wearer's skin. That is, skin care composition is either applied directly to one or more wearer contacting surfaces, or is applied to alternate locations or means such that the skin care composition is readily available for transfer from one or more wearer contacting surfaces during use without intervention by the user/caregiver. (For example, materials positioned beneath the wearer contacting surface, encapsulated compositions, etc.) Of course, to effectuate delivery of composition to those body regions most susceptible to skin disorders, it will be preferred to include the composition on the portion of the topsheet and cuffs that will contact the wearer's buttocks, genitals, intertriginous and anal regions during wear. Additionally, the composition may be applied to other article regions for delivery to one or more of the wearer's hips, abdomen, back, waist, sides, thighs, etc. Any of a variety of application methods that evenly distribute lubricious materials having a molten or liquid consistency can be used. Suitable methods include spraying, printing (e.g., flexographic printing), coating (e.g., contact slot coating, gravure coating), extrusion, or combinations of these application techniques, e.g. spraying the skin care composition on a rotating surface, such as a calender roll, that then transfers the composition to the desired portion of the article. The skin care composition can also be applied as a solid material via any of a variety methods, for example extrusion.

When applied to the article's topsheet, the manner of applying the composition to the article should be such that the topsheet does not become saturated with the composition, at least in the region corresponding to the liquid discharge region of the article, if the composition is hydrophobic in nature. If the topsheet becomes saturated with the composition in the liquid discharge region, there is a greater potential for the composition to block the topsheet openings, reducing the ability of the topsheet to transmit liquid to the underlying absorbent core. Also, saturation of the topsheet is not required to obtain the therapeutic and/or protective benefits. Similarly, saturation of other treated article components may not be necessary or desired to transfer sufficient composition for desired skin benefits. Particularly suitable application methods will apply the composition primarily to the outer surface of the diaper topsheet.

The minimum level of composition to be applied to the article's wearer-contacting surface is an amount effective for providing the therapeutic and/or protective benefits when the composition is delivered pursuant to the present methods. The level of composition applied will depend on various factors, including the article component treated, the relative amount of surface area of the wearer-contacting surface not treated with the composition, the composition's content and the like. In general, with compositions that are relatively hydrophobic and are to be applied to essentially all of the topsheet, the composition is preferably applied to the article topsheet in an amount ranging from about 0.1 mg/in$^2$ (0.016 mg/cm$^2$) to about 15 mg/in$^2$ (2.33 mg/cm$^2$), more preferably from about 1 mg/in$^2$ (0.16 mg/cm$^2$) to about 10 mg/in$^2$ (1.55 mg/cm$^2$). It will be recognized that higher levels of skin care composition may be applied to other article components where fluid handling properties are not impacted (e.g., cuffs, waist band, side panels, etc.). It will also be recognized that for compositions that are relatively hydrophilic, higher add-on levels may be used on the topsheet without adversely impacting liquid handling properties to an unacceptable degree. Conversely, higher levels of a hydrophilic composition may be undesired when applied to components (e.g., cuff, waist) other than the topsheet, to avoid wicking of exudates to the edges of the article which may result in leakage.

Because the composition is preferably substantially immobilized on the surface of the region treated, relatively small amounts of composition are needed to impart the desired skin care benefits. Applicants believe that the ability to use low levels to impart the desired skin benefits is due to the fact that pursuant to the methods described herein, composition is continuously, automatically delivered as articles are worn. As indicated, the ability to use relatively low levels of skin care composition, allows the article's topsheet to maintain its liquid transfer properties in the liquid discharge region.

The composition can be applied nonuniformly to the wearer contacting surface of the article. By "nonuniform" it is meant that the amount, location, pattern of distribution, etc. of the composition can vary over the wearer-contacting surface, and may further vary over specific regions of the article. For example, to maintain the liquid handling performance of the topsheet, it may be desired to apply the composition nonuniformly to the topsheet, particularly if the composition is hydrophobic in nature. In this regard, some portions of the treated surface of the article (and regions thereof) can have greater or lesser amounts of composition, including portions of the surface that do not have any composition on it. When the composition is relatively hydrophobic, in one such preferred embodiment the surface of the topsheet will have regions where no composition is applied, particularly in areas of the topsheet that correspond to the crotch region of the article. As used herein, the crotch region of the article is the rectangle, defined below, that is centered longitudinally and laterally about the article's crotch point. The "crotch point" is determined by placing the article on a wearer in a standing position and then placing an extensible filament around the legs in a figure eight configuration. The point in the article corresponding to the point of intersection of the filament is deemed to be the crotch point of the article. (It is understood that the crotch point is determined by placing the absorbent article on a wearer in the intended manner and determining where the crossed filament would contact the article.) With regard to incontinence devices (e.g., diapers, adult incontinent articles), the length of the crotch region corresponds to 40% of the absorbent article's total length (i.e., in the y-dimension). With regard sanitary napkins, the length of the crotch region corresponds to 80% of the absorbent article's total length. The width of the crotch region is equivalent to the width of the widest absorbent core component as measured at the crotch point. (As used herein, "absorbent core" components are those materials involved with acquiring, transporting, distributing and/or storing body liquids. As such, the term absorbent core does not include the topsheet or backsheet of the absorbent article.) By way of illustration, for an incontinent article having a length of 20 in. and a core width at the crotch point of 4 in., the crotch region is the rectangle, centered on the crotch point, having a length of 8 in. and a width of 4 in.

Surprisingly, while the topsheet or other components comprising the composition are treated nonuniformly (e.g., microscopic or macroscopic regions where no composition is applied), during wear of the article, the composition is transferred to the wearer even in regions of the skin corresponding to untreated regions within the topsheet or other components. The amount and uniformity of composition transferred to the skin is believed to depend on several factors, including, for example, application pattern of the skin care composition, contact of the wearer's skin to the treated article surface, friction created during wear time between the wearer's skin and the treated region, warmth generated from wearer to enhance the transfer of the composition, the composition's properties, the materials which constitute the composition, and the like.

Where the composition is applied nonuniformly, any pattern may be utilized, including, for example, application of small droplets (obtained via, e.g., spraying) discrete dots (obtained via, e.g., gravure printing), stripes that run in the longitudinal or lateral direction of the article (obtained via contact slot coating), spirals that run in the longitudinal or lateral direction, etc., patterned prints, etc. In those embodiments where the topsheet comprises discrete, untreated regions, the percent open area of the region of the topsheet that corresponds to the crotch region of the article can vary widely. (As referred to herein, the "percent open area" of the topsheet is determined by (i) measuring the surface area of the topsheet that overlies the crotch region, (ii) measuring the total surface area of the untreated region(s) in this portion of the topsheet and (iii) dividing the measurement in (ii) by the measurement in (i). As used herein, "untreated" means a region of the topsheet having less than about 0.01 mg/in$^2$ (0.0016 mg/cm$^2$) of the composition. In this regard, the percent open area may be from about 1% to about 99%, from about 5% to about 95%, from about 10% to about 90%, from about 15% to about 85%, from about 20% to about 80%, from about 25% to about 75%, from about 30% to about 70%, or from about 35% to about 65%. The percent open area required to achieve the desired composition effect and the desired liquid handling properties of the topsheet will be dictated largely by the characteristics of the composition (in particular the composition's contents and its relative hydrophobicity/hydrophilicy properties). One skilled in the art will appreciate that the desired percent open area will be readily determined through routine experimentation.

In general, with compositions that are relatively hydrophobic and are to be applied such that regions of the topsheet are not coated with the composition, the composition is preferably applied to the article topsheet in an amount ranging from about 0.05 mg/in$^2$ (0.0078 mg/cm$^2$) to about 35 mg/in$^2$ (5.43 mg/cm$^2$), more preferably from about 1 mg/in$^2$ (0.16 mg/cm$^2$) to about 25 mg/in$^2$ (3.88 mg/cm$^2$), still more preferably 4 mg/in$^2$ (0.62 mg/cm$^2$) to about 20 mg/in$^2$ (3.1 mg/cm$^2$). It will be recognized that for compositions that are relatively hydrophilic, higher add-on levels may be used without adversely impacting liquid handling properties of the topsheet to an unacceptable degree. Of course, for articles having relatively high percent open areas in the crotch, greater add-on levels may be obtainable without adversely affecting liquid handling by the topsheet.

In one preferred embodiment for carrying out the present methods, the topsheet of the articles utilized will comprise stripes of composition that run in the article's longitudinal direction. These longitudinal stripes (or spirals) are separated by longitudinal stripes where little or no composition is applied to the topsheet. In these embodiments, each stripe of composition will typically have a width of from about 0.1 in to about 0.75 in., more typically from about 0.1 in. to about 0.5 in., and the width of the stripes containing no composition will typically be from about 0.1 in. to about 1 in., more typically from about 0.15 to about 0.5 in. These ranges are applicable to typical infant diaper designs. For larger products such as adult incontinent products, these ranges may be higher.

Skin care composition can also be applied in nonuniform patterns on other article components. In these cases, the open area is calculated by the rectangle defined by the perimeters of the skin care composition.

The composition can be applied to the article at any point during assembly. For example, the composition can be applied to the finished disposable absorbent product before it has been packaged. The composition can also be applied to a given component (e.g., topsheet, cuffs, sides, waiste, etc.), at the converting site or by the material supplier, before it is combined with the other raw materials to form a finished disposable absorbent product. Again, the composition can be applied to other zones of the article such that the composition will migrate to one or more wearer contacting surfaces during use.

The composition is typically applied from a melt thereof to the article. Since in a preferred embodiment, the composition melts at significantly above ambient temperatures, it is usually applied as a heated composition to the article. Typically, the composition is heated to a temperature in the range from about 35° to about 150° C., preferably from 40° to about 100° C., prior to being applied to the article. Once the melted composition has been applied to the article, it is allowed to cool and solidify. Preferably, the application process is designed to aid in the cooling/set up of the composition.

In applying compositions to the articles, contact slot coating, spraying, gravure coating, extrusion coating methods are preferred. One such method involves slot coating of the composition on the article's topsheet after the topsheet is assembled with the other raw materials into a finished product.

VI. Test Methods

A. Evaluating Erythema and Rash

1. Test Summary

Two different infant diaper products are evaluated to determine if there is a difference in the frequency and/or severity of diaper rash and/or erythema in the diaper area in an average infant population associated with the use of a test product (i.e., comprising a skin care composition on one or more wearer contacting surface) over that associated with the control product (an equivalent product, with the exception that it contains no skin care composition).

2. Investigational Plan 2.1 Study Design

This study is conducted at a qualified clinical research organization (CRO) and should comply with good clinical practices (GCP) guidelines. The study is a randomized, double-blind, parallel group comparison clinical trial in which both the trained skin grader conducting skin evaluations and the caregivers of the panelists will be unaware of the treatment assignment of the study participants. A sufficient number of healthy infants will be recruited from the general population residing in the geographical area of the clinical site to participate and complete this study such that two hundred (200) infants, one hundred (100) per group, complete the study.

Two subject groups will participate in this study. Both groups will include healthy infants, each comprising approximately 50% males and 50% females. The two groups will be age and/or diaper size balanced (when wearing appropriately sized diapers). The two groups will consist of healthy infants not taking medications for conditions other than those that are routine for that age, such as common cold/flu. All infants will present Fitzpatrick scale skin type of I-III, and with no evidence of serious dermatological conditions (i.e., not atopic). (Fitzpatrick I-III skin types facilitate erythema grading.) Some level of erythema and diaper rash in the diaper region is permissible (defined under exclusion criteria below).

All infants who meet enrollment criteria will be assigned to use the control product for one week (baseline). At the end of one week, the infants will be randomly assigned into one of two possible groups: one group will remain on the control product for three weeks; the other group will use a test product for a period of three weeks. As such, the total duration of the test for both control and test product users is four weeks.

At the point when infants are randomized (Visit 2) into two groups, no further use of ointments, creams, lotions, corn starch, or powders will permitted on the skin in the diaper area during the remaining period of the study. The use of soap, water, baby wipes, or cleansing gels is permitted at diaper changes and baths.

The skin condition of infants will be evaluated at the following times: enrollment into the study (Visit 1); following one week baseline (Visit 2); twice per week for three weeks (Visits 3 through 8). Beginning with Visit 2, infants should be evaluated three hours (+/−15 minutes) after being changed into a fresh diaper. (Preferably, this change being the first after the overnight diaper.) After Visit 2, subsequent visits should occur three to four days apart.

2.2 Procedure:

Visit 1 (Enrollment)

A. Eligibility will be determined on the basis of the eligibility requirements listed below.

Figure 2A:
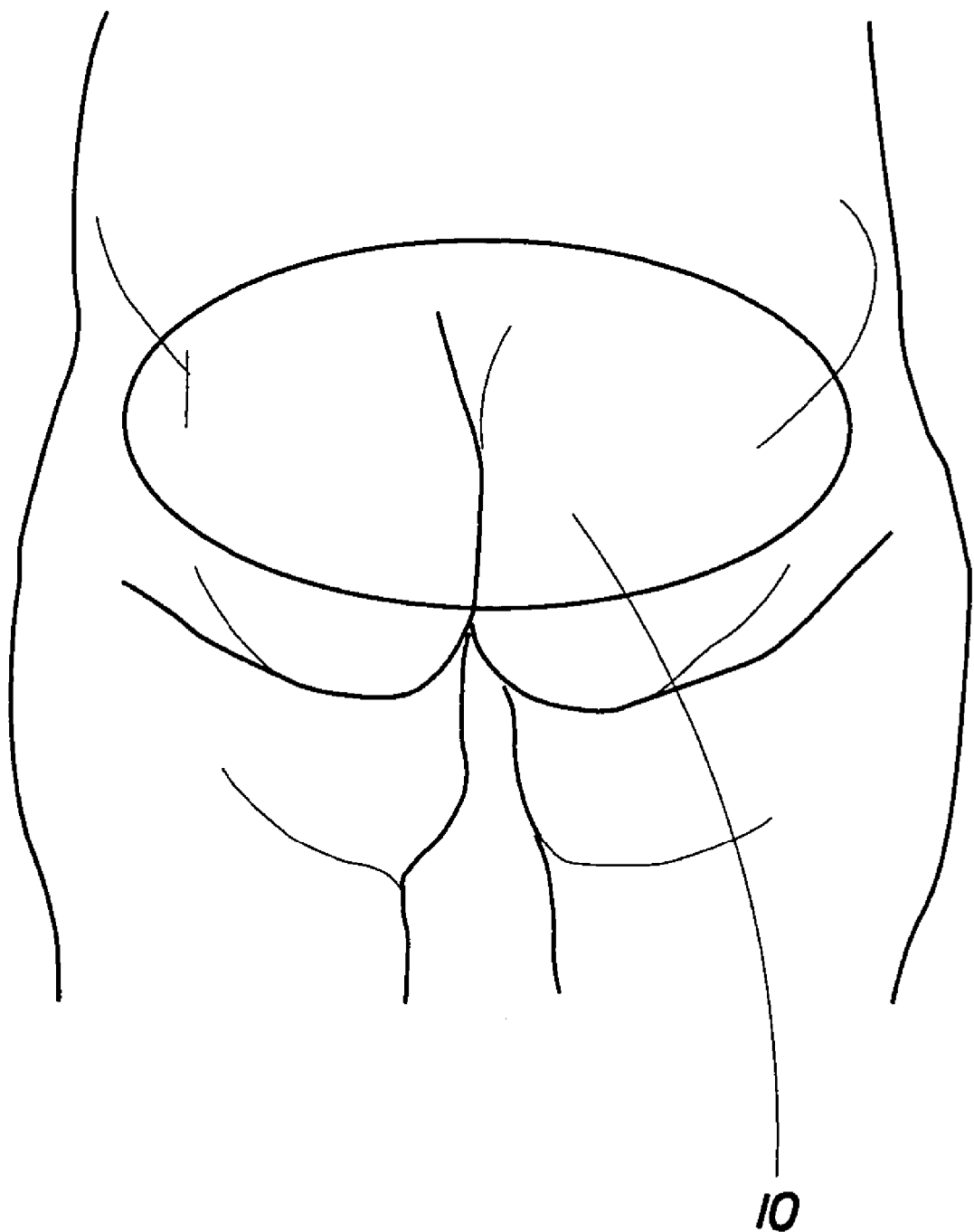
FIG. 2a through 2e depict the regions of a wearer of absorbent article that are assessed for rash and erythema.
Figure 2B:
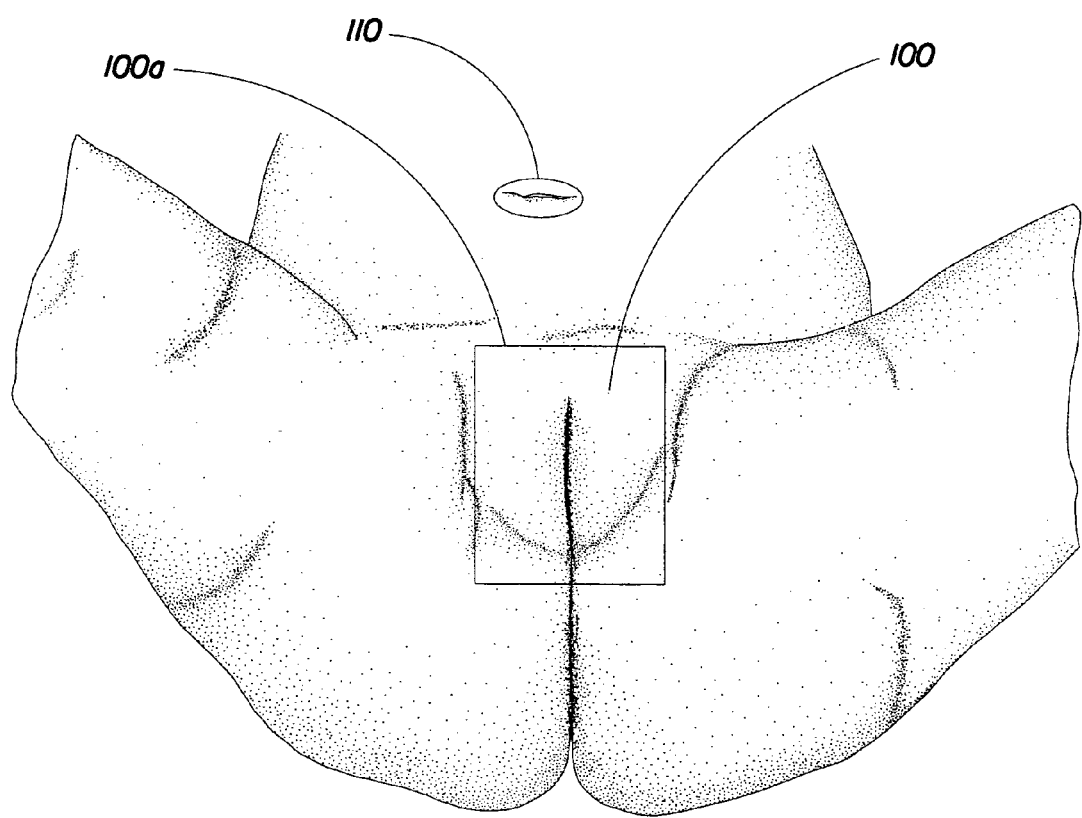
Figure 2C:
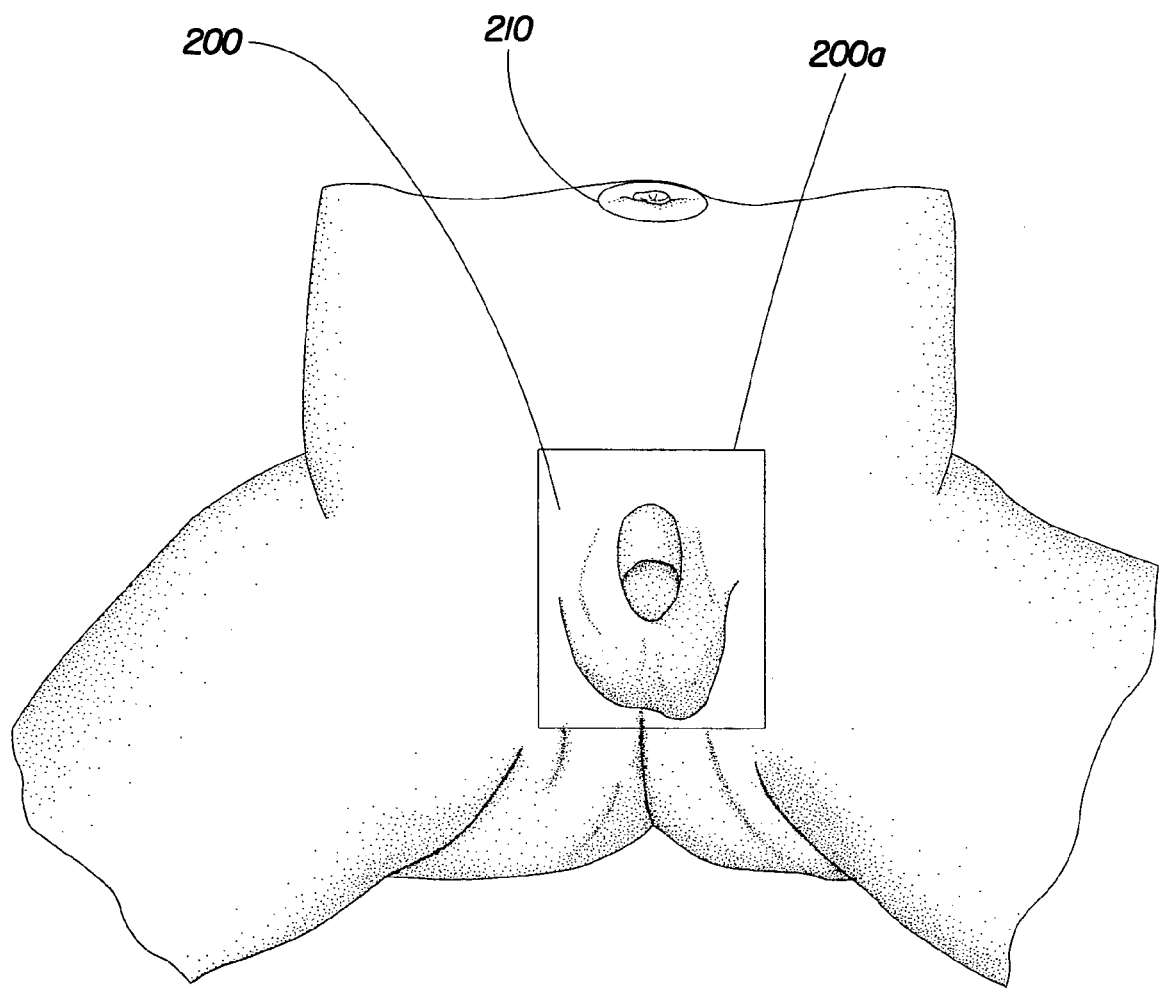
Figure 2D:
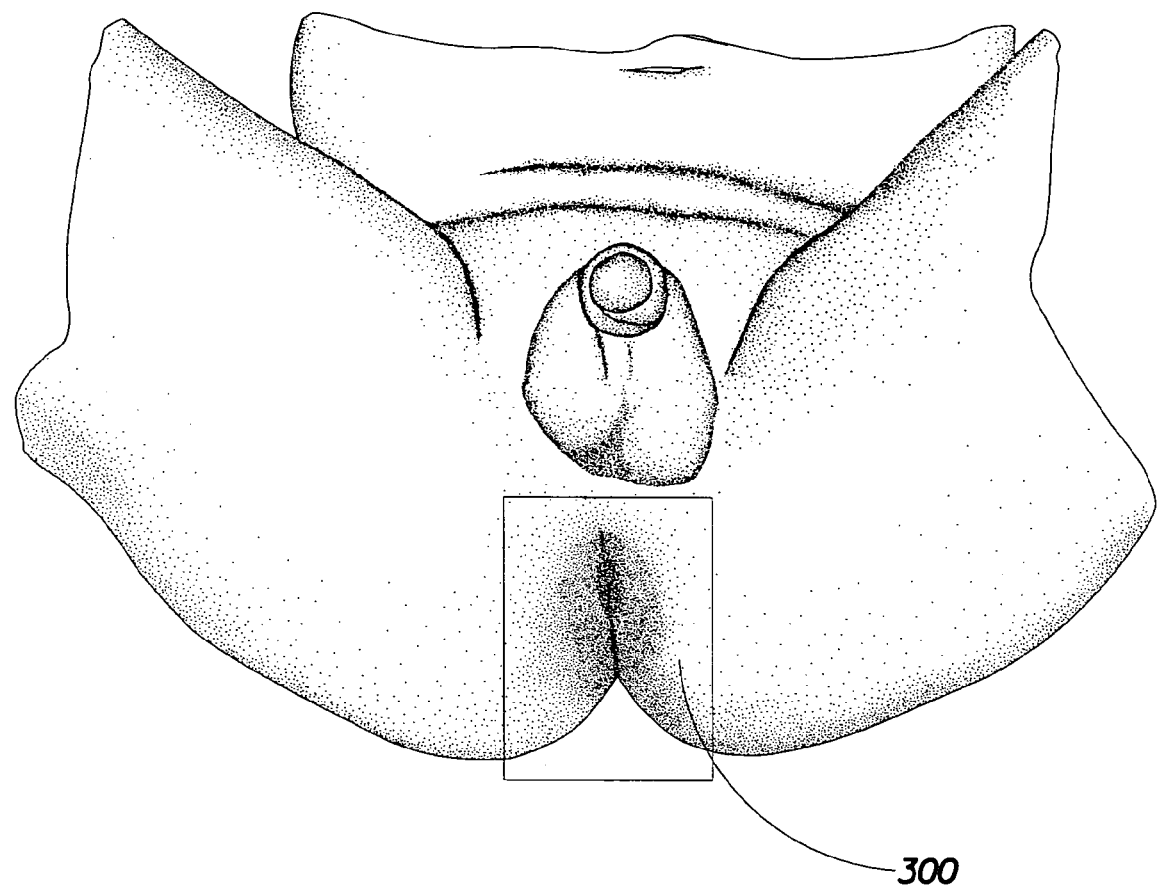
Figure 2E:
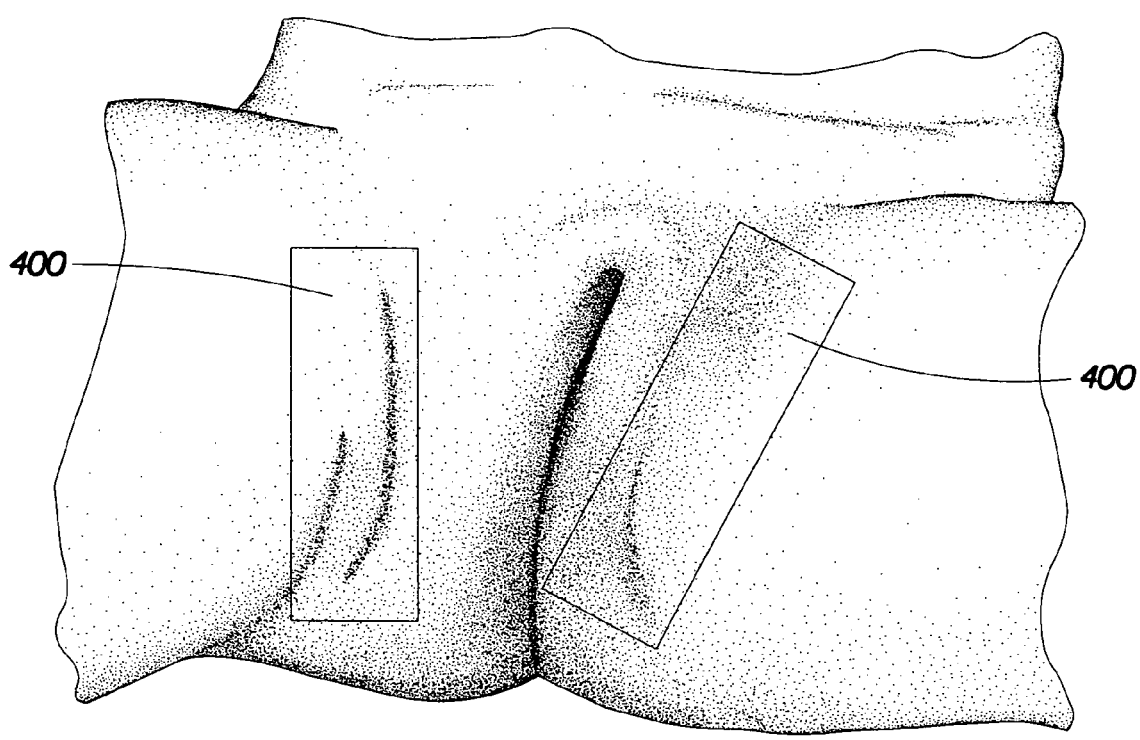

B. Erythema and diaper rash evaluations will be conducted at four sites in the diaper area (genitals, intertriginous, anal, and buttocks) to confirm acceptance of the infant into the test. Referring to FIGS. 2a, 2b, 2c, 2d, and 2e, the locations for grader assessment of erythema and rash are shown. FIG. 2a shows the region 10 of the buttocks for assessment in both male and female subjects. FIG. 2b shows region 100 of the genital area of a female subject for assessment of erythema and rash. FIG. 2b also shows navel 110 of a subject. For purposes of assessing erythema and rash in the genital area of a female subject, the upper portion of region 100, shown as line 100a, is approximately 1 inch above the top of the labial aperture. FIG. 2c shows region 200 of the genital area of a male subject for assessment of erythema and rash. FIG. 2c also shows navel 210 of a subject. For purposes of assessing erythema and rash in the genital area of a male subject, the upper portion of region 200, shown as line 200a, is approximately 1 inch above the top of the base of the penis. FIG. 2d shows the anal region 300 for assessment of erythema and rash in both male and female subjects. FIG. 2e shows regions 400 of the intertriginous area of both male and female subjects for assessment.

C. The parent/infant receives control product for the one week baseline.

Visit 2

A. The infant is brought to the test site wearing a diaper worn for three hour (+/−15 minutes).

B. The parent/infant proceeds to the skin grader for evaluations of skin erythema and rash at four sites in the diaper area (genitals, intertriginous, anal, and buttocks).

C. The infant is randomized into either the test or control group and given product and instructions to eliminate other lotion, creme, etc. use.

Visits 3 through 8

A. The infant is brought to the test site wearing a diaper worn for three hour (+/−15 minutes).

B. The parent/infant proceeds to the skin grader for evaluations of skin erythema and rash at four sites in the diaper area (genitals, intertriginous, anal, and buttocks).

C. Compliance with restriction on lotion, etc. is confirmed.

2.3 Study Population

As indicated, at least two hundred (200) infants are expected to complete this study. Two subject groups will participate in this study, each group comprising approximately 50% males and 50% females. The two groups will be age and/or diaper size balanced (when wearing appropriately sized diapers). The study population will consist of healthy infants not taking medications for conditions other than those that are routine for that age such as common cold/flu, with a Fitzpatrick scale skin type of I-III, and no evidence of serious dermatological conditions (e.g., not atopic). The presence of erythema and diaper rash is permissible.

2.3.1. Inclusion Criteria

Each Infant must:

a) have no serious dermatological conditions in the diaper area, b) be full time disposable diaper user, c) have a caregiver willing to not use lotions, creams, powders, or other skin preparations in the diaper area during the study.

The eligibility of each potential infant is also determined by the completion of a medical and dermatological history questionnaire. Subjects will be excluded from this study for one or more of the reasons listed below under exclusion criteria.

2.3.2 Exclusion Criteria

Babies are excluded from participation in the study if:
they do not meet the inclusion criteria.
at the first visit they have a diaper rash grade>2.5.
they have diabetes or chicken pox.
they have psoriasis, ichthyosis.
at Visit 1, they have a significant eruption in the diaper area and it is the opinion of the Clinical Research Organization's Principal Investigator or skin grader that the baby should be excluded.
use medication of any kind (e.g., oral antibiotics, antifungal agents, corticosteroids taken orally or topically applied to the skin), which in the opinion of the Clinical Research Organization's Principal Investigator and/or skin grader may have an influence on baby's skin in the diaper area.
they do not fit the diaper as determined at Visit 1.
they have any other medical condition that could compromise the study.
they have experienced diarrhea within the past four days.

2.4 Test Materials

The two treatment groups that will be included in this study are as follows:
Test Group: will use diapers having a skin care composition that is transferred to the wearer during use.
Control Group: will use equivalent diapers to the Test Group, but the diapers have no skin care composition that is transferred to the wearer during use.

2.5 Randomization and Regimen

Infants will be randomly assigned, using a statistically valid randomization schedule, at Visit 2 to either the test or control product group. The groups should be balanced for age or diaper size, sex, and diaper rash severity (e.g., mild, moderate, severe rash). Twins (or multiple births) will be assigned to use the same product.

2.6 Regimen & Compliance with Treatment

Each infant should arrive at the investigative site at approximately the same time of the day for each visit. The infants are expected to wear their assigned products only.

No ointments, creams, lotions, or powders should be used on the skin in the diaper area after visit 2. The use of soap, water, baby wipes, or cleansing gels is permitted at diaper changes.

Subjects should come to the site such that when their skin is evaluated they will have been wearing a product for three hours (+/−15 minutes). Preferably, this product is the one immediately following the overnight diaper. In the event of a bowel movement within the 3 hour time frame, the diaper should be changed as needed, and skin evaluation should proceed as scheduled.

2.7 Blinding

The test is a randomized, double-blind, parallel group comparison clinical trial in which a trained skin grader conducting skin evaluations, as well as the caregiver of the panelists, will be unaware of the treatment assignment of the study participants.

2.8 Subject Discontinuation/Termination

In addition to the exclusion criteria, a baby will be dropped from the study due to:
failure to appear for more than one visit,
medication that is required which will have a significant effect on the baby's skin condition in the diaper area,
they develop erythema or diaper rash>2.5 during the course of the study,
non-compliance—if they use their own diapers during the study, or if they use lotion, powders, etc.
any illness which the Clinical Research Organization's Principle Investigator decides may effect the results of the study.

2.9 Observations and/or Measurements

Skin evaluations will be conducted by a trained skin grader who will be blinded as to the assignment of treatments for each subject. The same grader should be used for all examinations. The grader should be experienced in evaluating infant skin conditions in the diapered region, especially diaper rash. Preferably, the grader will be a nurse. The grader will be separated from the area where the diapers are removed so that the grader will not see what diapers the babies are wearing.

At each examination period, each baby will be examined for erythema first, then diaper rash, at 4 locations on the body (genitals, intertriginous, anal, and buttocks).

Erythema and diaper rash severity will each be evaluated using the grading scales shown below. A pictorial description of the 4 diaper locations are shown in FIGS. 2a through 2e.

3. Statistical Methods 3.1 Planned Statistical Analyses

For purposes of the present disclosure, evidence of a test product improvement in rash or erythema is defined as a statistical or non-statistical (as defined above) difference at: (a) one or more of the 4 skin grading locations for the study group as a whole; or (b) one or more of the 4 skin grading locations for any gender or age or diaper size subset of the study group.

Baseline Visit will be defined as Visit 2; post-baseline visits will be defined as Visits 3 through 8. For all parameters, separate analyses will be done for each site. The same analyses will be done on the erythema (i.e., redness) severity grades as for the diaper rash severity grades. The primary comparison of interest is between the treatment groups.

The frequency of diaper rash (or erythema) will be analyzed in two ways. First, the presence of diaper rash (erythema) at any time during the course of the study will be evaluated. For each treatment group, the number and percentage of infants for which diaper rash (or erythema) was present (i.e., diaper rash severity grade is greater than 0 at any post-baseline visit) and absent (i.e., diaper rash severity grade equals 0 for every post-baseline visit) will be calculated. These dichotomous treatment group responses (i.e., presence and absence) will be analyzed using a chi-square test. The effects of sex or age or diaper size should be investigated using Mantel-Haenszel statistics or, if appropriate, a weighted least squares or loglinear categorical model.

The second way in which diaper rash (or erythema) frequency will be analyzed is to evaluate the number of post-baseline visits at which diaper rash (or erythema) was present for each subject (i.e., diaper rash grade greater than zero). The number of post-baseline visits with diaper rash (or erythema) will be analyzed using a loglinear Poisson regression model. The effects of sex or age or diaper size should be investigated by incorporating these effects into the model.

Diaper rash (or erythema) severity will be analyzed by evaluating average diaper rash (or erythema) severity over all post-baseline visits. For each subject, the average of all post-baseline visit diaper rash (or erythema) severity grades will be computed. These average severity grades will be analyzed using a one-way analysis of variance model. A transformation (e.g., log) may be done prior to analysis to improve the distributional characteristics of the averages (i.e., improve the homogeneity of the treatment group variances, improve the normality of the analysis of variance residuals). Alternatively, a nonparametric analog to the one-way analysis of variance may be done (e.g., Wilcoxon's Rank Sum Test) if the analysis of variance residuals do not adequately fit a normal distribution and/or the treatment group variances are not homogenous enough. The effects of sex or age or diaper size should be investigated by incorporating these effects into the analysis of variance model.

| ERYTHEMA GRADING SCALE | | |
|---|---|---|
| 0 | None | Skin is clear (may have some very slight dryness) |
| 0.5 | Slight | Faint to definite pink in a very small area (<2%) |
| 1.0 | Mild | Faint to definite pink in small area (2-10%) or Definite redness in very small area (<2%) |
| 1.5 | Mild/Mod | Faint to definite pink in larger area (>10%) or Definite redness in a small area (2-10%) or Very intense redness in very small area (<2%) |
| 2.0 | Moderate | Definite redness in larger area (10-50%) or Very intense redness in very small area (<2%) w/edema |
| 2.5 | | Mod/Severe Definite redness in very large area (>50%) or Very intense redness in small area (2-10%) w/edema |
| 3.0 | | Severe/Very intense redness in larger area (>10%) w/edema |

| RASH GRADING SCALE | | |
|---|---|---|
| 0 | None | Skin is clear (may have some very slight dryness and/or a single papule but no erythema) |
| 0.5 | Slight | Erythema: Faint to definite pink in a very small area (<2%) May also have a single Papule; and May also have: Skin Integrity: Some very slight dryness |
| 1.0 | Mild | Erythema: Faint to definite pink in small area (2-10%) or Definite redness in very small area (<2%) and/or Papules: A few scattered papules (2-5) May also have: Skin Integrity: Some slight dryness or scaling |
| 1.5 | Mild/Mod | Erythema: Faint to definite pink in larger area (>10%) or Definite redness in a small area (2-10%) or Very intense redness in a very small area (<2%) and/or Papules: Slightly scattered papules covering a single or multiple areas (<10%) May also have: Skin Integrity: Moderate dryness or scaling |
| 2.0 | Moderate | Erythema: Definite redness in large area (10-50%) or Very intense redness in very small area (2%) and/or Papules/Pustules: Single to several areas (10-50%) of papules, with 0-5 pustules May also have: Skin Integrity: Some slight desquamation or edema |
| 2.5 | Mod/Severe | Erythema: Definite redness in very large area (>50%) or Very intense redness in small area (2-10%) and/or Papules/Pustules: Larger areas (>50%) of multiple papules or numerous pustules or both and/or May also have: Skin Integrity: Moderate desquamation and edema |
| 3.0 | Severe | Erythema: Very intense redness in larger area (>10%) and/or Skin Integrity: severe desquamation, severe edema, erosion and ulceration May also have: Large areas of numerous confluent papules or Numerous pustules/vesicles |

B. Transfer of Skin Care Composition to Wearer's Skin

Overview

This method uses a removable skin analog material that is placed on a wearer's skin for a controlled period of time. After the skin analog has been removed, it is extracted using an appropriate solvent and the amount of skin care composition deposited thereon is determined using known analytical methods. The method is described for use with infant diapers comprising skin care compositions, as defined herein. One of skill in the art will recognize the appropriate changes for other skin care compositions, absorbent articles, or wearer types.

Subjects

Approximately equal numbers of male and female infants should be selected using the following inclusion and exclusion criteria. Sufficient infants should be selected to ensure that there are at least fifteen subjects per condition and transfer time who complete all aspects of the test.

Inclusion Criteria a. Healthy infant
b. Caregiver willing to not use lotions, creams, powders or other skin preparations in the diaper area for the duration of the test.
c. Infants who wear disposable diapers full time
d. Caregiver willing to give child bath the evening before the study and not again until after completion of the study
e. Caregiver will to have child refrain from swimming from the evening before the study until after completion of the study.
f. Preferably, infants who have infrequent bowel movements Exclusion Criteria a. The infant has been ill within the last four days
b. Diarrhea (soft stool) any time during the four days before the test
c. Medication which might increase frequency of bowel movements (e.g., oral antibiotics, anti fungal agents, corticosteroids)
d. Damaged skin in or around the test site (e. g., from sunburn, active dermal lesions, or the like)
e. Known allergies or irritation from adhesive or skin care ingredients Materials In Vivo Transfer Skin Analog: Dermatological Tape—TEGADERM Tape No. 1622W available from 3M Health Cares, St. Paul, Minn.
Sample Container Glass jar with closure available from VWR Scientific, West Chester, Pa. as catalog Number 15900-242
Tape Release Powder Baby powder (comprising only talc and fragrance) available from Johnson & Johnson, New Brunswick, N.J.
Surgical Gloves Available from Best Manufacturing Co., Menlo Ga., as product 6005PFM.

Extraction and Analysis

Extraction Solvent Dichloromethane, available from Sigma-Aldrich of St. Louis, Mo. as 27056-3
Stearyl alcohol Aldrich 25876-8
1-Hexadecanol Aldrich 25874-1
Dispensing Flask 10 ml
Gas Chromatograph Flame ionization Detector, Hewlett Packard Model 5890 is suitable.
Column Capillary column: Chrompack CP Sil-5 CB, 2 meters X 0.25 mm id, 0.12 micron film thickness fused silica capillary (no substitutions)

Instrumental Data System Must be able to reproducibly determine areas of peaks of interest.

Method

Figure 3A:
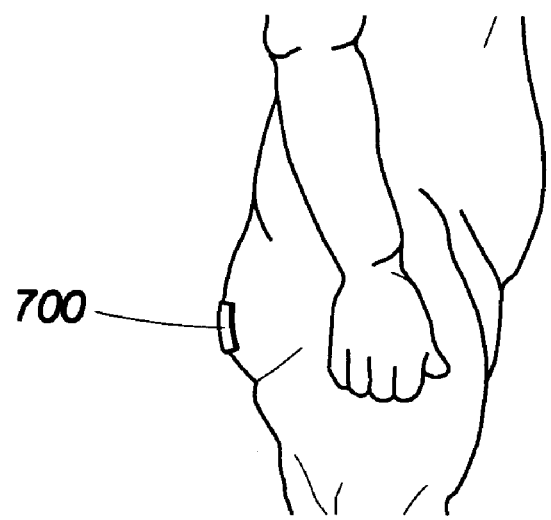
FIG. 3a is a side view showing placement of the skin analog used in the skin care composition transfer test.
Figure 3B:
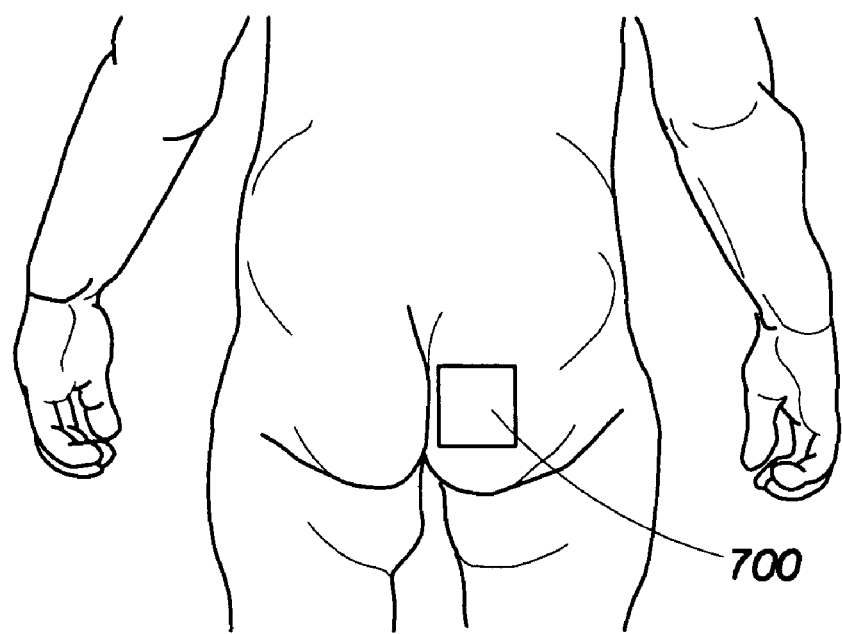
FIG. 3b is a plan view showing placement of the skin analog used in the skin care composition transfer test.

In Vivo Transfer
- A. Confirm from the subject's caregiver that the subject has been bathed within the last 24 hours and that no lotions, powders, etc. have been applied to the diapered region of the subject's skin since bathing.
- B. Wearing the surgical gloves, place the subject on the table and remove his/her diaper.
- C. Turn the subject on his/her stomach.
- D. Remove the release liner from a TEGADERM tape and lightly brush J&J Baby Powder over the adhesive surface (Wear surgical gloves, or the like, during application to prevent contamination of the tape). Provide sufficient powder such that there is a light coat of powder over all of the tape except the edges. (This step is done to keep the tape from adhering too aggressively to the child's skin.).
- E. FIGS. 3a and 3b illustrate placement location for the TEGADERM tape, shown in those figures as tape 700. Apply the tape 700 to the child's right buttock. The tape 700 is to be applied to the highest point on the child's buttock immediately adjacent to, but not in, the child's gluteal groove. A second tape 700 may be applied to measure transfer at two time increments or the effect of an additional diaper. If a second tape is used, apply the tape 700 on the left buttock using the procedure described above.
- F. Change diapers according to the following protocol: 3 hour transfer time—1 diaper; 6 hour transfer time—2 diapers (change at 3 hours); 24 hour transfer times ad lib by caregiver. For 24 hour transfer times the following additional instructions are to be followed:
  1. Use only water and a washcloth for cleaning the diapered area for the duration of the test. Do not use baby wipes. Avoid touching the area around the tapes with hands or any cleaning implement.
  2. Do not use skin care products (lotions, ointments, creams, soap, etc.) for the duration of the test.
  3. Do not bathe the subject for the duration of the test.
  4. Use only the test diapers. Record the time of each diaper change.
  5. Record the time of any bowel movement and clean the subject with water and a wash cloth.
- G. Record the time each diaper was applied for all test diapers.
- H. Recall the subject near the end of the predetermined transfer time.
- I. Remove the test diaper. If the child has had a bowel movement, the study personnel should remove the tape 700 and discard it (the subject has then completed the test and data from that subject are not included in the analysis). If the subject has urinated, the tape 700 will be acceptable for analysis as described below.
- J Test facility personnel should wear surgical gloves and remove the tape 700 by grasping the edge of the tape 700 with tweezers and gently peeling the remaining portion of the tape 700 from the skin.
- K. Place the used tape 700 in one of the glass jars and close the lid. Make sure the jar is properly labeled for subsequent sample identification.
- L. At the completion of the test collect all of the samples in the jars for analysis as described below.

Extraction and Analysis

This method is designed for use with the preferred skin care composition, the skin care composition of Table 1. One of ordinary skill in the art will recognize what adaptions may be necessary to extract and analyze the level of other skin care compositions. In principle: 1) one of the major ingredients of the composition is extracted from the skin analog using an appropriate solvent; 2) gas chromatographic or other appropriate quantitative analytical techniques are then used to determine the level of the major ingredient in the extract; 3) amount of skin care composition is calculated per unit area based on amount of major ingredient in extract and the area of the tape.

Internal Standard/Extraction Solvent

Prepare an internal standard/extraction solvent by accurately weighing 100±2 mg of 1-hexadecanol into a small beaker. Dissolve the 1-hexadecanol in dichloromethane and transfer to a 1 liter volumetric flask. Rinse the beaker 3 more times with dichloromethane transferring each rinse portion to the volumetric flask. Fill the volumetric flask to volume and mix well. This solution will be used to deliver the internal standard and extract skin care composition from the tapes. When not being used, this container should be kept tightly capped to prevent evaporation of solvent.

Calibration Standard

Prepare a calibration standard of known concentration by accurately weighing (±0.1 mg) 10±1 mg of the stearyl alcohol into a 100 ml volumetric flask. Record the weight of stearyl alcohol used. Add the internal standard/extraction solvent to the flask and mix to dissolve. Fill to volume and mix well. When not being used, this container should be kept tightly capped to prevent evaporation of solvent. This solution will be used to determine the relative response of the stearyl alcohol to the 1-hexadecanol internal standard for calibration of the instrument.

Preparation and Calibration of the Gas Chromatograph

All equipment should be installed, operated and maintained according to manufacturer's recommendations.

Install the column and check all the gas flows with the column oven at 100° C. and the injection port and detector at operating temperatures. The GC will be operated under the following conditions:

- Carrier Gas: Hydrogen (Helium may be used); flow rate 1.5 ml/min
- Injection Port: 325° C.; Split vent flow 30 ml/min; Septum purge 2 ml/min; straight through liner with glass wool plug; Merlin microseal.
- Injection volume: 2 µl split
- FID Detector: 350° C.; set gas flows according to manufacturer suggestions. Typical gas flows are 400 ml/minute for air, 30 ml/minute for hydrogen and 30 ml/minute for the auxiliary (make up) gas.
- Column Oven: 100° C. ramped at 15° C./minute to 325° C.; hold for 10 minutes Insure that all connections are tight and leak free. Ignite the detector and allow it to stabilize. Condition the column at 325° C. for 30 minutes. Clean the syringe with dichloromethane as needed. The syringe should also be rinsed with dichloromethane several times after each injection. Make several blank runs with injections of dichloromethane to ensure that a good baseline is obtained and that no extraneous peaks are present in the chromatogram. If extraneous peaks are present or baseline is not suitable, trouble shoot and correct problem(s).

Calibrate the instrument using the calibration standard prepared previously. Consult the data system manufacturer's instructions for the proper sequence of operations. Calculations should be performed in a manner similar to that described in CALCULATIONS below in order to provide the desired result.

Sample Analysis Procedure
1) Remove the lid from the sample jar and add 10 ml of the extraction solvent/internal standard solution using the dispensing flask. Replace the cap and swirl the contents to insure that the tape 700 is not adhering to the sides of the jar and is totally submersed in solvent. Repeat for all samples.
2) Allow the samples to sit 16 hours (typically done overnight).
3) Swirl the contents of the jar to mix. Using a transfer pipette, transfer an aliquot of the sample extract to a properly labeled autosampler vial. Cap the vial. Replace jar lid and retain until analyses are complete. Repeat for all samples.
4) Place the vials in the autosampler in random order and start the analyses using the GC conditions described above. The first vial should be a dichloromethane blank. Several "check" standards should be placed (about every 20th sample) through out the run to verify correct operation.
5) At the completion of the run, check each chromatogram to insure proper analysis. If a problem is suspected, trouble shoot and correct. Reanalyze samples as needed.

Calculations

The total micrograms of stearyl alcohol in each sample extract is calculated based on the relative response of the stearyl alcohol peak to that of the 1-hexadecanol internal standard. The ratio of the peak areas is multiplied by the relative response factor (determined at time of instrument calibration) and the micrograms of internal standard in the extract to yield the total μg of stearyl alcohol in a sample.

Instrument Calibration

Determine the instrumental relative response factor for the stearyl alcohol and the internal standard based on the areas of the stearyl alcohol and 1-hexadecanol peaks in the calibration standard chromatogram.

$$\text{Response factor}(R_f) = \frac{Area_{inst}}{weight_{inst}} \times \frac{weight_{sa}}{Area_{sa}} \times 10$$

where
$Area_{inst}$ GC peak area for the internal standard
$Area_{sa}$ GC peak area for the stearyl alcohol
$weight_{inst}$ micrograms of the internal standard used to prepare internal standard/extraction solvent
$weight_{sa}$ micrograms of the stearyl alcohol used to prepare the calibration standard Sample Calculations Calculate the total micrograms of stearyl alcohol in each sample using the peak areas from the sample chromatogram in the following equation:

$$\text{Total }^\mu g\ SA = \frac{Area_{sa}}{Area_{inst}} \times R_f \times \frac{weight_{inst}}{100}$$

where
$Area_{inst}$ GC peak area for the internal standard
$Area_{sa}$ GC peak area for the stearyl alcohol
$weight_{inst}$ micrograms of the internal standard used to prepare internal standard/extraction solvent Report amount of skin care composition transferred in mg/cm² where:

$$\text{Composition Transferred} = \frac{0.001 \times \mu g\ \text{of stearyl alcohol}}{\left(\begin{array}{c}\text{concentration of stearyl}\\ \text{alcohol in composition}\end{array}\right)} \times (\text{tape area})$$

For the method described above the concentration of stearyl alcohol in the composition is 41% and the tape patch measures 4.4 cm×4.4 cm.

Composition Transferred=(0.001×μg of stearyl alcohol)/(0.41×4.4 cm×4.4 cm) 0.000126×μg of stearyl alcohol (mg/cm²)

B. Water Vapor Transmission Rate Measurement

The Water Vapor Transmission Rate (WVTR) for the sample materials was calculated in accordance with ASTM Standard E96-80. Circular samples measuring three inches in diameter were cut from each of the test materials and a control which was a piece of CELGUARD® 2500 film from Hoechst Celanese Corporation of Sommerville, N.J. CELGUARD® 2500 film is a microporous polypropylene film. Five samples were prepared for each material. The test dish was a number 60-1 Vapomoter pan distributed by Thwing-Albert Instrument Company of Philadelphia, Pa. One hundred millimeters of water were poured into each Vapometer pan and individual samples of the test materials and control material were placed across the open tops of the individual pans. Screw-on flanges were tightened to form a seal along the edges of the pan, leaving the associated test material or control material exposed to the ambient atmosphere over a 6.5 centimeter diameter circle having an exposed area of approximately 33.17 square centimeters. The pans were placed in a forced air over at 100° F. (32° C.) for 1 hour to equilibrate. The oven was a constant temperature oven with external air circulating through it to prevent water vapor accumulation inside. A suitable forced air oven is, for example, a Blue M Power-O-Matic 60 oven distributed by Blue M Electric Company of Blue Island, Ill. Upon completion of the equilibration, the pans were removed from the oven, weighed and immediately returned to the oven. After 24 hours, the pans were removed from the oven and weighed again. The preliminary test water vapor transmission rate values were calculated as follows:

Test WVTR=(grams weight loss over 24 hours)×315.5 g/m²/24 hrs

The relative humidity within the oven was not specifically controlled.

Under predetermined set conditions of 100° F. (32° C.) an ambient relative humidity, the WVTR for the CELGUARD® 2500 control has been determined to be 5000 grams per square meter for 24 hours. Accordingly, the control sample was run with each test and the preliminary test values are corrected to set conditions using the following equation:

WVTR=(Test WVTR/control WVTR)×5000 g/m²/24 hrs. (g/m²/24 hrs)

VII. Specific Examples

The following are specific illustrations of (a) treating diaper topsheets with skin care compositions and (b) methods of the present invention which utilize articles comprising those topsheets. Similar approaches may be utilized to treat other components for providing treated articles for use in the present methods.

EXAMPLE I

Preparation of an Absorbent Article Having a Topsheet Comprising a Skin Care Composition A. Preparation of Skin Care Composition A skin care composition (Composition A) is made by mixing the following melted (i.e., liquid) components together: Petrolatum (available from Witco Corp., Greenwich, Conn.), Stearyl Alcohol (available from The Procter & Gamble Company, Cincinnati, Ohio as CO1897) and aloe extract (available from Madis Botanicals, Inc., South Hackensack, N.J. as Veragel Lipoid in Kaydol). The weight percentages of these components are shown in Table I below:

TABLE I

| Component | Weight % |
|---|---|
| Petrolatum | 58 |
| Stearyl Alcohol | 41 |
| Aloe | 1 |

B. Preparation of a Treated Article by Contact Slot Coating

Composition A is placed into a heated tank operating at a temperature of 170° F. The composition is subsequently applied with a contact applicator (using, for example, a Meltex EP45 hot melt adhesive applicator head having 5 slots and operating at a temperature of 170° F.) onto the topsheet of an article in a striped pattern where the stripes run in the article's longitudinal direction. Specifically, 5 stripes are applied, each stripe measuring 0.25 in. wide (i.e., in the articles lateral direction) and 11.75 in. long at an add-on level=7.7 mg/in$^2$ (12 g/m$^2$, 1.19 mg/cm$^2$). The distance between the stripes is 0.31 in.

The article to which skin care composition is added in this example is commercially available Pampers Premium (Size 4) diapers, available from Procter & Gamble, Cincinnati, Ohio.

EXAMPLE 2

Method of Improving Skin Health

An infant weighing 20 lbs who typically exhibits moderate diaper rash and erythema is diapered for a period of 21 days using the diaper of Example 1. The infant's diaper is changed according to the routine patterns of the caregiver. (Typical diapering patterns consist of changes every three to four hours during the day and application of a fresh diaper before overnight sleep.) No intervention by the caregiver, in the form of manual application of skin protective or moisture repellent products, occurs during this period. During the 21 day period, the subject is observed to have reduced severity of rash and erythema.

EXAMPLE 3

Method of Improving Skin Health

An active incontinent adult weighing 165 lbs. who constantly uses absorbent articles and who persistently has mild erythema uses an adult incontinent product analogous to the diaper of Example 1 for a period of at least about 5 days. The subject's article is changed according to the routine patterns of the user. (Typical changing patterns consist of changes every four to five hours during the day and application of a fresh article before overnight sleep.) No intervention by the user, in the form of manual application of skin protective or moisture repellent products, occurs during this period. At the end of the 5 day period, the subject is observed to have reduced or resolved erythema.

EXAMPLE 4

Method of Improving Skin Health

An infant weighing 32 lbs. exhibiting mild diaper rash and erythema is diapered for a period of at least about 5 days using the diaper of Example 1 during overnight sleep only. (That is, a untreated article is used throughout the day.) The infant's diaper is changed according to the routine patterns of the caregiver. No intervention by the caregiver, in the form of manual application of skin protective or moisture repellent products, occurs during this period. At the end of the 5 day period, the subject is observed to have reduced or resolved rash and erythema.

EXAMPLE 5

Method of Maintaining Skin Health

An infant weighing 25 lbs. exhibiting no diaper rash or erythema is diagnosed with otitis media and is prescribed a course of systemic antibiotics. Based on experience with conventional (untreated) diapers, the caregiver expects that the infant will develop erythema and/or diaper rash resulting from loose stools. As a result, diapers such as that described in Example 1 are used continuously throughout the period of administration of the antiobotic. No intervention by the caregiver, in the form of manual application of skin protective or moisture repellent products, occurs during this period. Throughout the period of antibiotic administration, the subject exhibits no erythema or diaper rash.

EXAMPLE 6

Breathable Films

Three breathable films with varying polymer blends were prepared and then each of the films were prepared. Each of the film formulations contained, on a total weight percent basis, 65% English China Supercoat calcium carbonate (CaCO$_3$) with a 1 micron average particle size and a 7 micron top cut. The calcium carbonate was obtained form ECCA Calcium Products, Inc. in Sylacauga, Ala., a division of ECC International. The calcium carbonate was blended with 15-25% by weight of linear low density polyethylene made from a blend of DOWLEX® 2517 linear low density polyethylene and DOWLEX® 2532 linear low density polyethylene blended in a weight ratio of 1:4 such that the melt indenx of the blend was 10 M.I. (/10 minutes at 190° F.). The DOWLEX® polymers are available from Dow Chemical U.S.A., Midland, Mich. The remaining 10-20% by weight of the formulation comprised Himont KS051P polypropylene-based polymer from Himont, USA of Wilmington, Del. The KS051P polymer is an olefinic thermoplastic elastomer or TPO multistep reactor product wherein an amorphous ethylene propylene random copolymer is molecularly dispersed in a predominately semi-crystalline high polypropylene monmer/low ethylene monomer continuous matrix. The amorphous component acts as the tacktifying or bonding agent as it begins to soften at about 55° C. As shown in Table I below, sample 1 contained 65% calcium carbonate, 10% KS051P polymer and 25% linear low density polyethylene. Sample 2 contained 65% calcium carbonate, 15% KS051P polymer and 20% linear low density polyethylene. The third sample contained 65% calcium carbonate, 20% KS051 P polymer and 15% linear low density polyethylene. Each of the three formulations were blown into films at a melt temperature of 375° F. (191° C.) at a blow up ratio of approximately 1.7 to produce films having an unstretched gauge of approximately 1.25 mils (50 gsm). Each of the films was subsequently stretched on a machine direction orientation (MDO) unit at a stretch ratio of 3× and at a temperature of 140° F. (60° C.). The resultant films were breathable as indicated by the water vapor transmission rate data set forth in Table II below and has basis weights of approximately 14 grams per square meter.

TABLE II

| SAMPLE | CaCO3 (% by weight) | LLDPE (% by weight) | KS051P (% by weight) | WVTR (g/m²/24 hr) |
|---|---|---|---|---|
| 1 | 65 | 25 | 10 | 4530 |
| 2 | 65 | 20 | 15 | 4300 |
| 3 | 65 | 15 | 20 | 3710 |

EXAMPLE 7

Breathable Films

In this Example, 65% by weight calcium carbonate and 30% by weight linear low density polyethylene were blended. As shown by Table III, to the basic blend there was added a series of recognized tacktifying or bonding agents in a weight percent of 5%. The bonding agents included REGALREZ® 1094, 3102 and 1126 bonding agents as well as ZONATAC® 501L and EASTMAN® 1023PL bonding agents. In addition, the film formulation from sample 2 of Example 6 was also formed into a film in the same fashion as described with respect to Example 6. Each of the films was blown at a blow-up ratio of 1.7 to a guage of approximately 1.5 mils (60 gsm). The films were stretched at 146° F. (63° C.) in the machine direction to three times (3×) their original length. This stretching temperature which was below the melting point (235° F./113° C.) of the predominately linear polyolefin polymers. The water vapor transmission rate for each of the films was measured. The results are presented in Table III below.

TABLE III

| Bonding Agent | Wt % | CaCO3 Wt % | LLDPE Wt % | WVTR (g/m²/24 hr) |
|---|---|---|---|---|
| KS050 | 1 | 65 | 20 | 4300 |
| REGALREZ ® 1094 | 5 | 65 | 30 | 2300 |
| REGALREZ ® 3102 | 5 | 65 | 30 | 3840 |
| REGALREZ ® 1126 | 5 | 65 | 30 | 3198 |
| ZONATAC ® 501L | 5 | 65 | 30 | 2990 |
| EASTMAN ® 1023PL | 5 | 65 | 30 | 4900 |

What is claimed is:

1. A disposable absorbent article which defines a front waist region, a rear waist region, and a crotch region which interconnects said front and rear waist regions, said absorbent article comprising:
   a) a vapor permeable backsheet
   b) a liquid pervious topsheet which is positioned in facing relation with said backsheet;
   c) an absorbent core located between said backsheet and said topsheet; and
   d) a skin care composition on at least a portion of a wearer-contacting surface of said absorbent article wherein the skin care composition comprises an emollient, a wax, and a viscosity increasing agent; wherein the emollient, the wax, and the viscosity increasing agent are different; and wherein the skin care composition has a viscosity from about 5 to about 500 centipoise and a zero-shear viscosity between about $1 \times 10^6$ and about $1 \times 10^8$ centipoise; further wherein the skin care composition is 2-50% liquid at 20° C., 25-95% liquid at 37° C., and has a final melting point $\geq 38°$ C.

2. The absorbent article of claim 1 wherein said viscosity increasing agent is selected from the group consisting of alkyl galactomannan, silica, talc, magnesium silicate, sorbitol, colloidal silicone dioxide, magnesium aluminum silicate, zinc stearate, sesquioleate, cetyl hydroxy ethyl cellulose and other modified celluloses, and mixtures thereof.

3. The absorbent article of claim 1 wherein said emollient is selected from the group consisting of sucrose ester fatty acids, fatty acid esters, alkyl ethoxylates, fatty acid ester ethoxylates, polysiloxanes, fatty alcohol ethers, polyethylene glycol and derivatives thereof, propoxylated fatty alcohols, fatty esters of polyhydroxy alcohols, and mixtures thereof.

4. The absorbent article of claim 1 wherein said emollient is a petroleum-based emollient.

5. The absorbent article of claim 1 wherein said wax is selected from the group consisting of carnauba, ozokerite, candelilla, ceresin, esparto, ouricuri, rezowax, isoparaffin, other mined and mineral waxes, and mixtures thereof.

* * * * *